(12) United States Patent
Fujita et al.

(10) Patent No.: US 9,696,290 B2
(45) Date of Patent: Jul. 4, 2017

(54) METHOD FOR FRACTIONATING DIOXINS

(71) Applicant: MIURA CO., LTD., Matsuyama-shi, Ehime (JP)

(72) Inventors: Hiroyuki Fujita, Matsuyama (JP); Hirofumi Nakamura, Matsuyama (JP)

(73) Assignee: MIURA CO., LTD., Matsuyama-shi (JP)

(*) Notice: Subject to any disclaimer, the term of this patent is extended or adjusted under 35 U.S.C. 154(b) by 0 days.

(21) Appl. No.: 14/768,327

(22) PCT Filed: May 27, 2013

(86) PCT No.: PCT/JP2013/064614
§ 371 (c)(1),
(2) Date: Aug. 17, 2015

(87) PCT Pub. No.: WO2014/192056
PCT Pub. Date: Dec. 4, 2014

(65) Prior Publication Data
US 2016/0011163 A1 Jan. 14, 2016

(51) Int. Cl.
*G01N 33/03* (2006.01)
*B01D 15/08* (2006.01)
(Continued)

(52) U.S. Cl.
CPC .............. *G01N 33/03* (2013.01); *B01D 15/08* (2013.01); *B01D 15/12* (2013.01);
(Continued)

(58) Field of Classification Search
CPC ........ G01N 33/03; B01D 15/20; B01D 15/08; B01D 15/12; B01D 15/206
See application file for complete search history.

(56) References Cited

U.S. PATENT DOCUMENTS

| 2002/0035303 A1 | 3/2002 | Chu et al. |
| 2005/0287037 A1 | 12/2005 | Honda et al. |
| 2009/0107213 A1* | 4/2009 | Honda ..................... B01J 20/08 73/23.37 |

FOREIGN PATENT DOCUMENTS

| CN | 1721836 A | 1/2006 |
| CN | 102062762 A | 5/2011 |

(Continued)

OTHER PUBLICATIONS

Extended European Search Report including opinion dated Mar. 29, 2016, issued in the corresponding European Patent Application No. 13885973.1.

*Primary Examiner* — Krishnan S Menon
*Assistant Examiner* — Dwan A Gerido
(74) *Attorney, Agent, or Firm* — Birch, Stewart, Kolasch & Birch, LLP

(57) ABSTRACT

The interior of a fractionating tool for fractionating dioxins is packed with a purification layer and an adsorption layer. The adsorption layer includes a first adsorption layer including an activated carbon-containing silica gel layer and a graphite-containing silica gel layer, and a second adsorption layer including an alumina layer. When a solution of dioxins is injected into the purification layer and is supplied with an aliphatic hydrocarbon solvent, the solvent dissolves dioxins in the solution of dioxins and passes through the purification layer and the adsorption layer. In this process, non-ortho PCBs, PCDDs and PCDFs among dioxins are adsorbed to the first adsorption layer, and mono-ortho PCBs among dioxins are adsorbed to the second adsorption layer. As a result, dioxins are fractionated into a group including non-ortho PCBs, PCDDs and PCDFs, and mono-ortho PCBs.

6 Claims, 5 Drawing Sheets

(51) Int. Cl.
　　　*B01J 20/08*　　　　(2006.01)
　　　*B01J 20/20*　　　　(2006.01)
　　　*B01D 15/18*　　　　(2006.01)
　　　*B01J 20/32*　　　　(2006.01)
　　　*B01J 20/10*　　　　(2006.01)
　　　*B01J 20/28*　　　　(2006.01)
　　　*B01D 15/12*　　　　(2006.01)
　　　*B01D 15/20*　　　　(2006.01)

(52) U.S. Cl.
　　　CPC ....... *B01D 15/1871* (2013.01); *B01D 15/206* (2013.01); *B01J 20/08* (2013.01); *B01J 20/103* (2013.01); *B01J 20/20* (2013.01); *B01J 20/28052* (2013.01); *B01J 20/3236* (2013.01); *B01J 2220/42* (2013.01); *B01J 2220/54* (2013.01)

(56) References Cited

FOREIGN PATENT DOCUMENTS

| | | | |
|---|---|---|---|
| CN | 102539548 | A | 7/2012 |
| JP | 2001-305119 | A | 10/2001 |
| JP | 2001-330597 | * | 11/2001 |
| JP | 2001-330597 | A | 11/2001 |
| JP | 2002-40007 | A | 2/2002 |
| JP | 2002040007 | * | 2/2002 |
| JP | 2005-172758 | A | 6/2005 |
| JP | 2005-214816 | A | 8/2005 |
| JP | 2006-84276 | A | 3/2006 |
| JP | 2007-225283 | A | 9/2007 |
| JP | 2008-297388 | A | 11/2008 |

\* cited by examiner

METHOD FOR FRACTIONATING DIOXINS

TECHNICAL FIELD

The present invention relates to a method for fractionating dioxins, in particular, to a method for fractionating dioxins contained in an aliphatic hydrocarbon solvent solution of dioxins.

BACKGROUND ART

Out of concern for environmental pollution by dioxins which are strongly toxic substances, it is required in various countries to analyze and evaluate contamination by dioxins with respect to exhaust gases from waste incineration facilities, the atmospheric air, water such as plant effluent or river water, fly ash generated in waste incineration facilities and soil. Such analysis and evaluation are often required also for foods.

The term "dioxins" generally encompasses polychlorinated dibenzo-para-dioxins (PCDDs), polychlorinated dibenzofurans (PCDFs) and dioxin-like polychlorinated biphenyls (DL-PCBs). Among 209 kinds of polychlorinated biphenyls (PCBs), DL-PCBs are PCBs showing toxicity similar to those of PCDDs and PCDFs, and include non-ortho PCBs and mono-ortho PCBs.

In evaluating contamination by dioxins for samples including environmental samples such as the atmospheric air and soil, and food samples, first, it is necessary to extract dioxins from the sample to obtain an analytical sample. When the sample is a solid such as soil or a solid food, dioxins are extracted from the solid, for example, by a Soxhlet extraction method. When the sample is a fluid such as the atmospheric air or a beverage, for example, dioxins in the fluid are trapped by using a collector such as a filter, and then the collector is washed or subjected to a Soxhlet extraction method to extract the dioxins collected thereby. The extract of dioxins obtained in accordance with the above manners is subjected as an analytical sample to quantitative analysis by using an analyzer such as a gas chromatography mass spectrometry (GC/MS).

The extract of dioxins contains various impurities that can influence on the analysis result, for example, polychlorinated polycyclic aromatic hydrocarbons resembling dioxins in chemical structures and chemical behavior such as polychlorinated diphenyl ether (PCDE) and PCBs other than DL-PCBs (hereinafter, also referred to as non-DL-PCBs). Therefore, the extract is normally concentrated as appropriate after subjected to purification, and then applied to the analyzer. As a method for purifying the extract, Patent Literature 1 discloses a method of using a chromatograph column equipped with a primary column packed with sulfuric acid silica gel and silver nitrate silica gel as purifying agents, and a secondary column packed with activated carbon-containing silica gel or graphite carbon as an adsorbing agent. In this method, as an adsorbing agent of the secondary column, activated carbon-containing silica gel or graphite carbon can be selectively used, and when both of these adsorbing agents are used, they may be used in a layered state or in a mixed state.

In the purification treatment method using this chromatograph column, first, an extract of dioxins is injected into the primary column, and then the primary column is supplied with a hydrocarbon solvent. The hydrocarbon solvent dissolves dioxins in the injected extract, and passes through the primary column and the secondary column. During the passage, dioxins dissolved in the hydrocarbon solvent pass through the purifying agent of the primary column, and are adsorbed to the adsorbing agent of the secondary column. On the other hand, impurities contained in the extract are dissolved in the hydrocarbon solvent together with dioxins, and partially degraded while they are passing through the purifying agent of the primary column, and partially adsorbed. Among the impurities or the degradation products thereof, those not adsorbed in the purifying agent pass through the adsorbing agent of the secondary column in the state of being dissolved in the hydrocarbon solvent and are then discharged from the column.

Next, the primary column and the secondary column are separated, and the secondary column is supplied with an alkylbenzene capable of dissolving dioxins. By collecting the alkylbenzene passing through the secondary column, it is possible to obtain an impurities-free alkylbenzene solution of dioxins. This alkylbenzene solution can be used as an analytical sample for dioxins, and is subjected to analysis by an analyzer such as a GC/MS after appropriate concentration.

In such a purification treatment method, all kinds of dioxins contained in the extract are adsorbed to the adsorbing agent in the secondary column, and the adsorbed dioxins are extracted with alkylbenzene. Therefore, in the analyzer, all kinds of dioxins contained in the alkylbenzene solution are analyzed at once.

However, in analysis of an alkylbenzene solution containing all kinds of dioxins at once, the obtainable result can be unreliable. For example, it is known that when the alkylbenzene solution is analyzed by a high-resolution GC/MS, mono-ortho PCBs influence on quantitative analysis results of PCDDs and PCDFs, and inversely PCDDs and PCDFs influence on quantitative analysis results of mono-ortho PCBs.

For this reason, in analysis of dioxins, an attempt has been made to prepare an analytical sample by fractionating dioxins into several kinds. For example, Patent Literature 2 discloses a method of using graphite-like carbon or a mixture of graphite-like carbon and other materials such as silica gel, activated carbon-containing silica gel, activated carbon, alumina or zeolite as an adsorbing agent for dioxins.

In this method, a column packed with an adsorbing agent is supplied with a purified dioxins solution to cause dioxins to be adsorbed to the adsorbing agent. Then, the column is sequentially supplied with several kinds of solvents to prepare several kinds of solutions of dioxins. Patent Literature 2 states that this method makes it possible to prepare, for example, three kinds of solutions of dioxins: a solution containing PCBs other than DL-PCBs, a solution containing mono-ortho PCBs, and a solution containing non-ortho PCBs, PCDDs and PCDFs.

However, in this method, it is difficult to finely fractionate dioxins because all kinds of dioxins are to be adsorbed to the adsorbing agent as is the case with the method described in Patent Literature 1. For example, part of PCDDs and PCDFs can be mixed into the solution containing mono-ortho PCBs, and part of mono-ortho PCBs can be mixed into the solution containing non-ortho PCBs, PCDDs and PCDFs.

PRIOR ART LITERATURES

Patent Literatures

Patent Literature 1: Japanese Patent Laid-open Publication No. 2002-40007
Patent Literature 2: Japanese Patent Laid-open Publication No. 2006-297368

SUMMARY OF THE INVENTION

Problems to be Solved by the Invention

The present invention intends to fractionate dioxins into a dioxin group including non-ortho PCBs, PCDDs and PCDFs, and mono-ortho PCBs with high accuracy.

Means for Solving the Problems

A method for fractionating dioxins according to the present invention includes the step of passing an aliphatic hydrocarbon solvent solution of dioxins through an activated carbon-containing silica gel layer and a graphite-containing silica gel layer in this order.

In the fractionating method, when the aliphatic hydrocarbon solvent solution of dioxins passes through the activated carbon-containing silica gel layer and the graphite-containing silica gel layer in this order, a dioxin group including non-ortho PCBs, PCDDs and PCDFs among dioxins is adsorbed to the activated carbon-containing silica gel layer or the graphite-containing silica gel layer. On the other hand, mono-ortho PCBs among dioxins remain in the aliphatic hydrocarbon solvent solution, and pass through the activated carbon-containing silica gel layer and the graphite-containing silica gel layer. As a consequence, dioxins in the aliphatic hydrocarbon solvent solution are fractionated into a dioxin group including non-ortho PCBs, PCDDs and PCDFs adsorbed to the activated carbon-containing silica gel layer or the graphite-containing silica gel layer, and mono-ortho PCBs remaining in the aliphatic hydrocarbon solvent solution.

In one embodiment of the fractionating method of the present invention, the aliphatic hydrocarbon solvent solution having passed through the graphite-containing silica gel layer is further passed through an alumina layer.

In this case, when the aliphatic hydrocarbon solvent solution having passed through the activated carbon-containing silica gel layer and the graphite-containing silica gel layer passes through the alumina layer, the remaining mono-ortho PCBs are adsorbed to the alumina layer. As a consequence, dioxins in the aliphatic hydrocarbon solvent solution are fractionated into a dioxin group including non-ortho PCBs, PCDDs and PCDFs adsorbed to the activated carbon-containing silica gel layer or the graphite-containing silica gel layer, and mono-ortho PCBs adsorbed to the alumina layer.

The fractionating method of this embodiment may further include the steps of supplying the activated carbon-containing silica gel layer and the graphite-containing silica gel layer through which the aliphatic hydrocarbon solvent solution has passed with a solvent capable of dissolving dioxins, to secure the solvent having passed through the activated carbon-containing silica gel layer and the graphite-containing silica gel layer, and supplying the alumina layer through which the aliphatic hydrocarbon solvent solution has passed with a solvent capable of dissolving dioxins, to secure the solvent having passed through the alumina layer.

When the fractionating method includes these steps, the dioxin group including non-ortho PCBs, PCDDs and PCDFs adsorbed to the activated carbon-containing silica gel layer or the graphite-containing silica gel layer and the mono-ortho PCBs adsorbed to the alumina layer are dissolved in the solvents supplied respectively and extracted, and thus obtained as separate extracts.

The present invention according to another aspect relates to a method for preparing a sample for analyzing dioxins contained in a solution of dioxins. The preparation method includes the steps of adding the solution of dioxins to a purification layer including a silver nitrate silica gel layer and a sulfuric acid silica gel layer, supplying the purification layer to which the solution of dioxins has been added with an aliphatic hydrocarbon solvent, passing the aliphatic hydrocarbon solvent having passed through the purification layer through an activated carbon-containing silica gel layer and a graphite-containing silica gel layer in this order, passing the aliphatic hydrocarbon solvent having passed through the graphite-containing silica gel layer through an alumina layer, supplying the alumina layer through which the aliphatic hydrocarbon solvent has passed with a solvent capable of dissolving dioxins, to secure the solvent having passed through the alumina layer as a first analytical sample, and supplying the activated carbon-containing silica gel layer and the graphite-containing silica gel layer through which the aliphatic hydrocarbon solvent has passed with a solvent capable of dissolving dioxins, to secure the solvent having passed through the activated carbon-containing silica gel layer and the graphite-containing silica gel layer as a second analytical sample.

In this preparation method, when the purification layer to which the solution of dioxins has been added is supplied with an aliphatic hydrocarbon solvent, the aliphatic hydrocarbon solvent passes through the purification layer. In this process, dioxins and impurities contained in the solution of dioxins are dissolved in the aliphatic hydrocarbon solvent. Then, some of the impurities are degraded as a result of reaction with the silver nitrate silica gel layer or the sulfuric acid silica gel layer of the purification layer. Also, some of the impurities and a degradation product are adsorbed to the silver nitrate silica gel layer or the sulfuric acid silica gel layer. On the other hand, dioxins pass through the purification layer in the condition of being dissolved in the aliphatic hydrocarbon solvent. As a result, dioxins are separated from part of the impurities.

Regarding the aliphatic hydrocarbon solvent dissolving dioxins having passed through the purification layer, a dioxin group including non-ortho PCBs, PCDDs and PCDFs among dioxins is adsorbed to the activated carbon-containing silica gel layer or the graphite-containing silica gel layer when the solvent passes through the activated carbon-containing silica gel layer and the graphite-containing silica gel layer in this order, and mono-ortho PCBs among dioxins are adsorbed to the alumina layer when the solvent passes through the alumina layer. Therefore, the first analytical sample can be a sample for analyzing mono-ortho PCBs, and the second analytical sample can be a sample for analyzing the dioxin group including non-ortho PCBs, PCDDs and PCDFs. In other words, according to this preparation method, it is possible to separately prepare the analytical sample for mono-ortho PCBs, and the analytical sample for the dioxin group including non-ortho PCBs, PCDDs and PCDFs.

In the preparation method, it is generally preferred that the solution of dioxins is added to the silver nitrate silica gel layer of the purification layer.

The present invention according to still another aspect relates to a method for analyzing dioxins contained in a solution of dioxins. The analyzing method includes the step of analyzing a first analytical sample and a second analytical sample prepared by the preparation method of the present invention by a gas chromatography method or a bioassay method.

The analyzing method is capable of analyzing mono-ortho PCBs with high accuracy by analysis of the first analytical sample, and is also capable of analyzing non-ortho PCBs, PCDDs and PCDFs with high accuracy by analysis of the second analytical sample.

Other objects and results of the present invention will be mentioned in the following detailed description.

EMBODIMENTS OF THE INVENTION

With reference to the drawings, embodiments of a method for preparing an analytical sample according to the present invention will be described below. Each drawing illustrates an outline of an example of an apparatus or a fractionating tool for use in conducting a preparation method of the present invention, and does not accurately reflect the structure, shape, size and the like of each part.

First Embodiment

Figure 1:
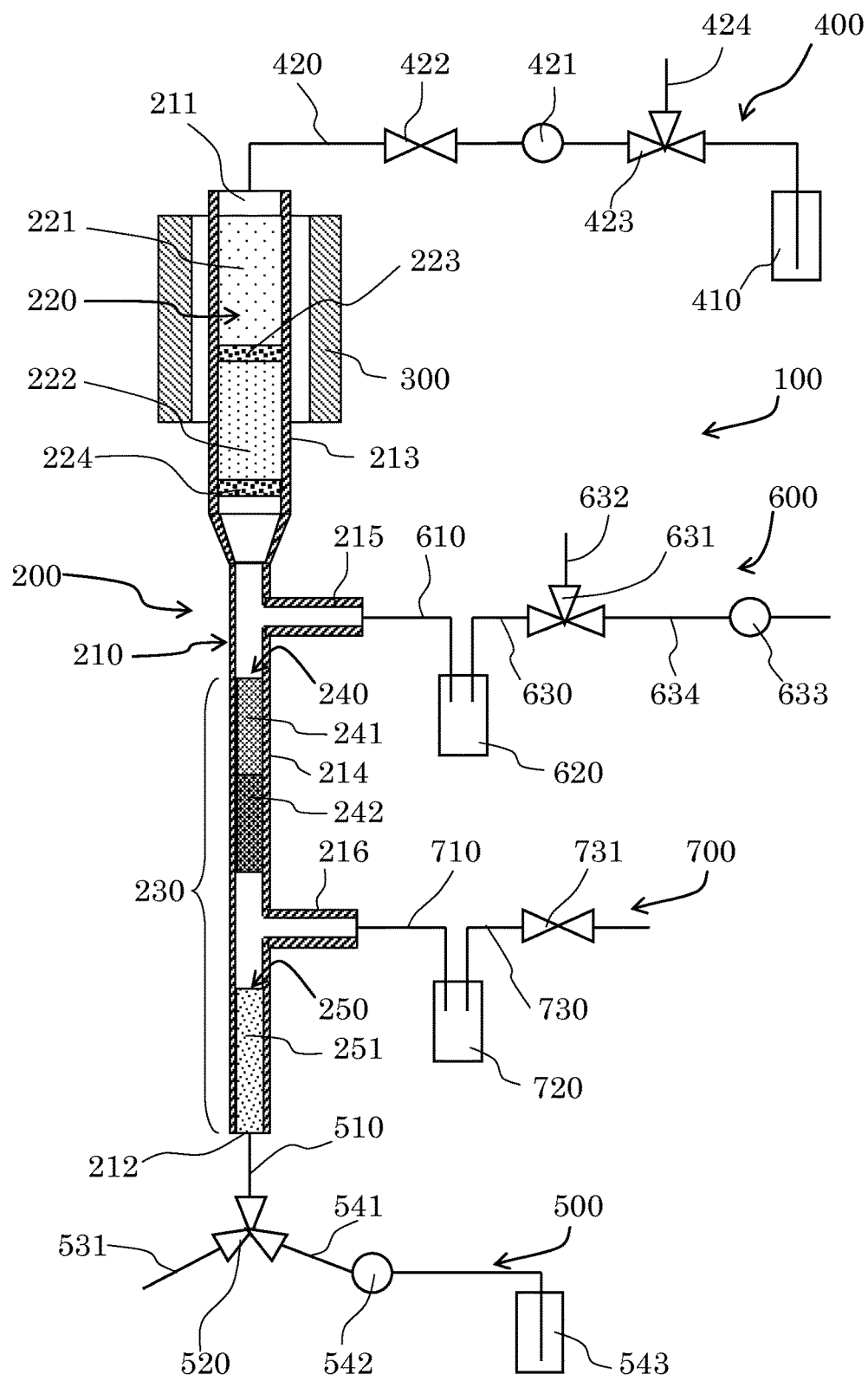
FIG. 1 A partial section view of an outline of a first example of an apparatus for conducting a method for preparing an analytical sample according to the present invention.

Referring to FIG. 1, the first example of an apparatus capable of conducting a method for preparing an analytical sample according to the present invention will be described. In FIG. 1, a preparation device 100 is provided for preparing an analytical sample of dioxins from a solution of dioxins, and mainly includes a fractionating tool 200 for dioxins, a heating device 300, a solvent supplying device 400, a solvent outflow pathway 500, a first extraction pathway 600 and a second extraction pathway 700.

The fractionating tool 200 includes a tubular body 210. The tubular body 210 is formed of a material having at least solvent resistance, chemical resistance and heat resistance, for example, glass, a resin or a metal having these characteristics, and is formed into a sequence of cylinder opening at both ends having an opening 211 at its one end and an opening 212 at its other end. The tubular body 210 has a large-diameter portion 213 having a relatively large diameter, formed on the side of the opening 211, and a small-diameter portion 214 having a relatively small diameter, formed on the side of the opening 212. The small-diameter portion 214 has two branch channels as openings, namely a first branch channel 215 and a second branch channel 216 disposed with a distance therebetween.

The tubular body 210 is held in a standing position, and its interior is packed with a purification layer 220 and an adsorption layer 230.

The purification layer 220 is packed in the large-diameter portion 213, and is multiple silica gel layers in which a silver nitrate silica gel layer 221, a first active silica gel layer 223, a sulfuric acid silica gel layer 222 and a second active silica gel layer 224 are arranged in this order from the side of the opening 211.

The silver nitrate silica gel layer 221 is made up of silver nitrate silica gel, and is provided for degrading or adsorbing some impurities mixed into a solution of dioxins. The silver nitrate silica gel used herein is prepared by uniformly adding an aqueous solution of silver nitrate on the surface of particulate silica gel (typically, active silica gel whose activity is enhanced by heating) having a particle size of about 40 to 210 μm and then removing moisture by heating under reduced pressure. Typically, the amount of the aqueous silver nitrate solution added to the silica gel is set preferably in the range of 5 to 20% of the weight of the silica gel.

While packing density of the silver nitrate silica gel in the silver nitrate silica gel layer 221 is not particularly limited, it is typically set preferably in the range of 0.3 to 0.8 g/cm$^3$, and more preferably in the range of 0.4 to 0.7 g/cm$^3$.

The sulfuric acid silica gel layer 222 is made up of sulfuric acid silica gel, and is provided for degrading or adsorbing some impurities contained along with dioxins in a solution of dioxins. The sulfuric acid silica gel used herein is prepared by uniformly adding concentrated sulfuric acid on the surface of particulate silica gel (typically, active silica gel whose activity is enhanced by heating) having a particle size of about 40 to 210 μm. Typically, the amount of concentrated sulfuric acid added to the silica gel is set preferably in the range of 10 to 130% of the weight of the silica gel.

While packing density of the sulfuric acid silica gel in the sulfuric acid silica gel layer 222 is not particularly limited, it is typically set preferably at 0.3 to 1.1 g/cm$^3$, and more preferably at 0.5 to 1.0 g/cm$^3$.

The first active silica gel layer 223 is provided to prevent the silver nitrate silica gel layer 221 and the sulfuric acid silica gel layer 222 from directly coming into contact with each other to result in mutual chemical reaction, and is made up of particulate silica gel having a particle size of about 40 to 210 μm. The silica gel used herein may have appropriately increased activity by heating.

The second active silica gel layer 224 is made up of silica gel similar to that of the first active silica gel layer 223, and is provided for adsorbing some impurities degraded by reaction with the sulfuric acid silica gel layer 222 and degradation products thereof as well as sulfuric acid eluted from the sulfuric acid silica gel layer 222, and preventing them from moving toward the adsorption layer 230.

In the purification layer 220, as to the ratio between the silver nitrate silica gel layer 221 and the sulfuric acid silica gel layer 222, the weight ratio of the sulfuric acid silica gel layer 222 to the silver nitrate silica gel layer 221 is preferably set at 1.0 to 50 times, and more preferably at 3.0 to 30 times. When the weight ratio of the sulfuric acid silica gel layer 222 is more than 50 times, the proportion of the silver nitrate silica gel layer 221 is relatively small, so that in the purification layer 220, the ability to adsorb the impurities contained in the solution of dioxins can be insufficient. Contrarily, when the weight ratio of the sulfuric acid silica gel layer 222 is less than 1.0 time, the ability to degrade the impurities contained in the solution of dioxins can be insufficient in the purification layer 220.

The adsorption layer 230 is provided for fractionating dioxins contained in a solution of dioxins, and includes a first adsorption layer 240 including an activated carbon-containing silica gel layer 241 and a graphite-containing silica gel layer 242, and a second adsorption layer 250 including an alumina layer 251. The first adsorption layer 240 and the second adsorption layer 250 are packed in the small-diameter portion 214 with a space therebetween. Specifically, the first adsorption layer 240 is packed in the small-diameter portion 214 between the first branch channel 215 and the second branch channel 216, and the second adsorption layer 250 is packed in the small-diameter portion 214 between the second branch channel 216 and the opening 212.

The activated carbon-containing silica gel layer 241 of the first adsorption layer 240 is disposed on the side of the purification layer 220 in the first adsorption layer 240, and is made up of a mixture of activated carbon and particulate silica gel. Such a mixture may be activated carbon-dispersed silica gel obtainable by simply mixing activated carbon and silica gel, or may be activated carbon-embedded silica gel obtainable by reacting a mixture of sodium silicate (water glass) and activated carbon with mineral acid. As the activated carbon, any commercially available products may be used, however, typically particulate or powder materials having a particle size of about 40 to 100 μm, and having a specific surface area measured by the BET method of 100 to 1,200 $m^2$/g, and particularly 500 to 1,000 $m^2$/g are preferred. As the silica gel in the activated carbon-dispersed silica gel, the one similar to that in the first active silica gel layer 223 is used.

The proportion of activated carbon in the mixture of activated carbon and silica gel is preferably 0.013 to 5.0% by weight, and more preferably 0.1 to 3.0% by weight. When the proportion of activated carbon is less than 0.013% by weight or more than 5.0% by weight, the ability to adsorb PCDDs having a large number of chlorine atoms, and PCDFs having a large number of chlorine atoms can be deteriorated in the first adsorption layer 240.

While packing density of the activated carbon-containing silica gel layer 241 is not particularly limited, it is typically set preferably at 0.3 to 0.8 g/$cm^3$, and more preferably at 0.45 to 0.6 g/$cm^3$.

The graphite-containing silica gel layer 242 of the first adsorption layer 240 is disposed adjacent to the activated carbon-containing silica gel layer 241 in the first adsorption layer 240, and is made up of a mixture obtainable by simply mixing graphite and particulate silica gel. As the graphite, any commercially available products may be used, however, typically particulate or powder materials having a particle size of about 40 to 200 μm, and having a specific surface area measured by the BET method of 10 to 500 $m^2$/g, and particularly 50 to 200 $m^2$/g are preferred. As the silica gel, the one similar to that in the first active silica gel layer 223 is used.

The proportion of graphite in the mixture of graphite and silica gel is preferably 2.5 to 50% by weight, and more preferably 5 to 25% by weight. When the proportion of graphite is less than 2.5% by weight, the ability to adsorb non-ortho PCBs can be deteriorated in the first adsorption layer 240. Contrarily, when the proportion of graphite is more than 50% by weight, non-DL-PCBs, in particular, non-DL-PCBs having 1 to 2 chlorine atoms can be more likely to be adsorbed in the first adsorption layer 240.

While packing density of the graphite-containing silica gel layer 242 is not particularly limited, it is typically set preferably at 0.2 to 0.6 g/$cm^3$, and more preferably at 0.3 to 0.5 g/$cm^3$.

In the first adsorption layer 240, the ratio between the activated carbon-containing silica gel layer 241 and the graphite-containing silica gel layer 242 is set preferably 1:1 to 1:12, and more preferably 1:1 to 1:9 by the volume ratio (A:B) between the layer 241 (A) and the layer 242 (B). When the proportion of the activated carbon-containing silica gel layer 241 is smaller than the proportion defined by the above volume ratio, the ability to adsorb part of PCDDs and PCDFs, in particular, both PCDDs and PCDFs having 8 chlorine atoms can be deteriorated in the first adsorption layer 240. Contrarily, when the proportion of the activated carbon-containing silica gel layer 241 is larger, mono-ortho PCBs can be more likely to be adsorbed in the first adsorption layer 240.

The alumina layer 251 of the second adsorption layer 250 is made up of particulate alumina. The alumina used herein may be any one of basic alumina, neutral alumina and acidic alumina.

The activity of the alumina is not particularly limited. A preferred particle size of alumina is typically 40 to 300 μm.

While packing density of alumina in the alumina layer 251 is not particularly limited, it is typically set preferably at 0.5 to 1.2 g/$cm^3$, and more preferably at 0.8 to 1.1 g/$cm^3$.

The size of the fractionating tool 200 can be appropriately set in accordance with the amount of a solution of dioxins to be treated by the preparation device 100, and is not particularly limited. However, for example, when the amount of a solution of dioxins is about 1 to 20 mL, the large-diameter portion 213 is preferably designed to have an inner diameter of 10 to 20 mm and a length of about 100 to 300 mm in the portion in which the purification layer 220 can be packed, and the small-diameter portion 214 is preferably designed to have an inner diameter of 3 to 10 mm and a length of about 20 to 80 mm in the portion in which the first adsorption layer 240 can be packed and a length of about 20 to 80 mm in the portion in which the second adsorption layer 250 can be packed.

The heating device 300 is disposed to surround the outer periphery of the large-diameter portion 213, and is provided for heating the purification layer 220 with respect to the silver nitrate silica gel layer 221 and the first active silica gel layer 223, as well as part of the sulfuric acid silica gel layer 222, namely, the part neighboring the silver nitrate silica gel layer 221.

The solvent supplying device 400 has a first solvent supplying pathway 420 extending toward the tubular body 210 from a first solvent container 410. The first solvent supplying pathway 420 can be attached to/detached from the opening 211 of the tubular body 210, and is capable of airtightly closing the opening 211 when it is attached to the opening 211. The first solvent supplying pathway 420 has an air introducing valve 423, a first pump 421 for supplying the tubular body 210 with a solvent reserved in the first solvent container 410, and a first valve 422 in this order from the side of the first solvent container 410. The air introducing valve 423 is a three way valve having an air introducing channel 424 opening at one end, and is provided for switching the flow channel between the air introducing channel 424 side and the first solvent container 410 side. The first valve 422 is a two way valve provided for switching between opening and closing of the first solvent supplying pathway 420.

The solvent reserved in the first solvent container 410 can dissolve dioxins, and is typically an aliphatic hydrocarbon solvent, preferably an aliphatic saturated hydrocarbon solvent having 5 to 8 carbon atoms. Examples thereof include n-pentane, n-hexane, n-heptane, n-octane, isooctane and cyclohexane. These solvents may be used as a mixture as appropriate.

The solvent outflow pathway 500 has a flow channel 510 that is airtightly connected to the opening 212 of the tubular body 210. The flow channel 510 has a second valve 520. The second valve 520 is a three way valve communicating with a disposal pathway 531 through which the solvent from the tubular body 210 is disposed of, and a second solvent supplying pathway 541 for supplying the tubular body 210 with a solvent, and is provided for switching the flow channel 510 to communicate with either one of the disposal pathway 531 and the second solvent supplying pathway 541.

The second solvent supplying pathway 541 has a second pump 542, and communicates with a second solvent container 543 reserving a solvent for extracting dioxins trapped by the fractionating tool 200. The extraction solvent reserved in the second solvent container 543 can be selected according to the analytical method for dioxins as will be described later. When a gas chromatography method is employed as the analytical method, solvents suited for the method, for example, toluene or benzene may be used. Also, a mixed solvent obtained, for example, by adding an aliphatic hydrocarbon solvent or an organic chlorine solvent to toluene or benzene can be used. When the mixed solvent is used, the proportion of toluene or benzene is set at 50% by weight or higher. Examples of the aliphatic hydrocarbon solvent used in the mixed solvent include n-pentane, n-hexane, n-heptane, n-octane, isooctane and cyclohexane. Examples of the organic chlorine solvent include dichloromethane, trichloromethane and tetrachloromethane. Among these extraction solvents, toluene is particularly preferred because dioxins can be extracted from the fractionating tool 200 with the use of a small amount thereof.

When a bioassay method is employed as the analytical method, solvents suited for the method, for example, a hydrophillic solvent such as dimethyl sulfoxide (DMSO) or methanol is used.

The first extraction pathway 600 has a first recovery pathway 610 extending from the first branch channel 215. The first recovery pathway 610 airtightly communicates with the first branch channel 215 at its one end, and is airtightly inserted into a first recovery container 620 for recovering a solvent at its other end. In the first recovery container 620, one end of a first ventilation pathway 630 is airtightly inserted separately from the first recovery pathway 610. The first ventilation pathway 630 has a third valve 631 at its other end. The third valve 631 is a three way valve, to which an open channel 632 opening at one end, and an air supply pathway 634 having a compressor 633 for sending compressed air to the first ventilation pathway 630 communicate, and is provided for switching the first ventilation pathway 630 to communicate with either one of the open channel 632 and the air supply pathway 634.

The second extraction pathway 700 has a second recovery pathway 710 extending from the second branch channel 216. The second recovery pathway 710 airtightly communicates with the second branch channel 216 at its one end, and is airtightly inserted into a second recovery container 720 for recovering a solvent at its other end. In the second recovery container 720, one end of a second ventilation pathway 730 is airtightly inserted separately from the second recovery pathway 710. The second ventilation pathway 730 has a fourth valve 731. The fourth valve 731 is a two way valve, and is provided for switching between opening and closing of the second ventilation pathway 730.

Next, a method for preparing an analytical sample of dioxins by using the above-described preparation device 100 will be described. First, in the preparation device 100, the first valve 422, the air introducing valve 423, the second valve 520, the third valve 631 and the fourth valve 731 are set at predetermined initial states. To be more specific, the first valve 422 is set to be in the open state, and the air introducing valve 423 is set to communicate to the side of the first solvent container 410. The second valve 520 is set so that the flow channel 510 communicates with the disposal pathway 531. Further, the third valve 631 is set so that the first ventilation pathway 630 and the air supply pathway 634 communicate with each other, and the fourth valve 731 is set to be in the close state.

The preparation method for the analytical sample mainly includes a fractionating step and an extracting step as follows.

<Fractionating Step of Dioxins>

After setting the initial state, a solution of dioxins is injected into the fractionating tool 200. Here, the first solvent supplying pathway 420 is removed from the tubular body 210, and the solution of dioxins is injected to the purification layer 220 through the opening 211. Then, after restoring the first solvent supplying pathway 420 to the tubular body 210, the heating device 300 is actuated to heat part of the purification layer 220, namely, the entire silver nitrate silica gel layer 221 and first active silica gel layer 223, and part of the sulfuric acid silica gel layer 222.

The solution of dioxins injected herein is an extract prepared by extracting dioxins by using a solvent from a sample possibly containing dioxins such as an environmental sample including the atmospheric air and soil, or a food sample. However, an oily food possibly containing dioxins, for example an oil obtained from fish (fish oil), itself may be used. Such a solution of dioxins often contains polychlorinated polycyclic aromatic hydrocarbons such as PCDE and non-DL-PCBs that resemble dioxins in chemical structure and chemical behavior and can influence on the analytical result of dioxins, as impurities.

In the case of an extract from a soil sample, the extract often contains paraffins (straight-chain hydrocarbon compounds) contained in the soil in a considerable amount, as impurities. Paraffins are easily adsorbed to carbon-based adsorbing agents along with PCDDs, PCDFs and non-ortho PCBs, and are easily extracted from the adsorbing agents together with PCDDs, PCDFs and non-ortho PCBs. Therefore, they are known as causative substances for lock mass fluctuation that influences on the analytic accuracy in the case of analyzing dioxins by GC/MS method, in particular, by GC-HRMS method.

Typically, the extract of dioxins can be directly injected into the fractionating tool 200 as far as the extract is based on an aliphatic hydrocarbon solvent. When the extract is obtained by extraction using an organic solvent other than an aliphatic hydrocarbon solvent, for example an aromatic hydrocarbon solvent such as toluene, the extract can be injected into the fractionating tool 200 by replacing the aromatic hydrocarbon solvent used for extraction with an aliphatic hydrocarbon solvent. Typically, the aliphatic hydrocarbon solvent used for extraction or solvent replacement is preferably an aliphatic hydrocarbon solvent having 5 to 10 carbon atoms, for example, n-hexane, isooctane, nonane and decane. In particular, inexpensive n-hexane is preferred.

Generally, the injection amount of a solution of dioxins into the fractionating tool 200 is preferably about 1 to 10 mL. The solution to be injected may be concentrated by distilling off part of the solvent.

When a solution of dioxins is an oily substance such as fish oil, the solution of dioxins may be injected into the fractionating tool 200 together with an aliphatic hydrocarbon solvent capable of dissolving the same, or as a solution obtained by preliminarily dissolving the same in the solvent.

In this case, the solution of dioxins and the aliphatic hydrocarbon solvent are adjusted so that the total amount is equal to the above-described injection amount.

The injected solution of dioxins permeates into an upper part of the silver nitrate silica gel layer 221 and is heated by the heating device 300 together with part of the purification layer 220. The heating temperature by the heating device 300 is set at 35° C. or higher, preferably 50° C. or higher, and more preferably 60° C. or higher. By this heating, some impurities contained along with dioxins in the solution of dioxins react with the purification layer 220 and are degraded. When the heating temperature is less than 35° C., the reaction between the impurities and the purification layer 220 is less likely to advance, and part of the impurities can be more likely to remain in the analytical sample of dioxins. The upper limit of the heating temperature is not particularly limited. However, typically, it is preferably less than or equal to the boiling temperature from the view point of the safety.

The reaction between the silver nitrate silica gel layer 221 and the sulfuric acid silica gel layer 222 during heating is suppressed as they are stacked with the first active silica gel layer 223 interposed therebetween.

Next, after a lapse of 10 to 60 minutes from the start of heating, the fractionating tool 200 is supplied with a solvent from the solvent supplying device 400. At this time, the heating device 300 may be kept operating or may be stopped. In this step, the first pump 421 is actuated while the first valve 422 is set in the open state, to supply an appropriate amount of the solvent reserved in the first solvent container 410 into the tubular body 210 through the opening 211 via the first solvent supplying pathway 420. This solvent dissolves dioxins, degraded products of impurities, and impurities remaining undegraded (non-DL-PCBs are included in the impurities) contained in the solution of dioxins, and passes through the purification layer 220 as an aliphatic hydrocarbon solvent solution containing dioxins. In this process, part of the degraded products and impurities are adsorbed to the silver nitrate silica gel layer 221, the first active silica gel layer 223, the sulfuric acid silica gel layer 222 and the second active silica gel layer 224. The solvent passing thorough the purification layer 220 is naturally cooled when it passes through the part not heated by the heating device 300, namely, a lower part of the sulfuric acid silica gel layer 222 and the second active silica gel layer 224.

The solvent having passed through the purification layer 220 flows into the adsorption layer 230, passes through the first adsorption layer 240 and the second adsorption layer 250, flows into the flow channel 510 through the opening 212, and is then disposed of through the disposal pathway 531. In this process, dioxins contained in the solvent from the purification layer 220 are adsorbed to the adsorption layer 230 and thus separated from the solvent. In the adsorption layer 230, non-ortho PCBs, PCDDs and PCDFs among dioxins are adsorbed to the first adsorption layer 240, and mono-ortho PCBs are adsorbed to the second adsorption layer 250. Therefore, dioxins contained in the solvent are fractionated into a dioxin group including non-ortho PCBs, PCDDs and PCDFs and mono-ortho PCBs in the adsorption layer 230.

Impurities contained in the solvent having passed through the purification layer 220 are partly disposed of together with the solvent after passing through the adsorption layer 230 and are partly adsorbed to the adsorption layer 230. For example, non-DL-PCBs and PCDE are adsorbed to the second adsorption layer 250 together with mono-ortho PCBs. On the other hand, paraffins pass through the adsorption layer 230 and are disposed of through the disposal pathway 531.

<Extracting Step of Dioxins>

Next, dioxins adsorbed to the adsorption layer 230 are extracted with a solvent to prepare an analytical sample of dioxins. Prior to this preparation, in the preparation device 100, the purification layer 220 and the adsorption layer 230 are subjected to a drying treatment. Here, first, the air introducing valve 423 of the solvent supplying device 400 is switched to the air introducing channel 424 side. Then, the first pump 421 is actuated to aspirate air from the air introducing channel 424.

The air aspirated from the air introducing channel 424 is supplied into the tubular body 210 through the opening 211 via the first solvent supplying pathway 420, and then it flows into the flow channel 510 through the opening 212 after passing through the purification layer 220 and the adsorption layer 230, and is then discharged through the disposal pathway 531. In this process, the solvent remaining in the purification layer 220 is pushed out by the passing air, and passes through the adsorption layer 230, and is then discharged from the disposal pathway 531 together with the air. As a result, the purification layer 220 undergoes a drying treatment.

Next, the first pump 421 is stopped and the first valve 422 is switched into the closed state, and the compressor 633 is actuated in the first extraction pathway 600.

By operation of the compressor 633, compressed air is supplied to the first branch channel 215 from the air supply pathway 634 through the first ventilation pathway 630, the first recovery container 620 and the first recovery pathway 610. The compressed air passes through the adsorption layer 230, and flows into the flow channel 510 through the opening 212, and is then discharged through the disposal pathway 531. In this process, the solvent remaining in the layers of the adsorption layer 230 is pushed out by the compressed air, and is discharged from the disposal pathway 531 together with the compressed air. As a result, each layer of the adsorption layer 230 undergoes a drying treatment.

In the first step for preparing an analytical sample of dioxins, the compressor 633 is stopped, and the fourth valve 731 of the second extraction pathway 700 is switched into the open state. Also, in the solvent outflow pathway 500, the second valve 520 is switched so that the flow channel 510 communicates with the second solvent supplying pathway 541, and the second pump 542 is actuated. In this manner, an appropriate amount of solvent reserved in the second solvent container 543 is supplied into the tubular body 210 through the opening 212 via the second solvent supplying pathway 541 and the flow channel 510.

The solvent supplied into the tubular body 210 passes through the second adsorption layer 250 and flows into the second branch channel 216, and is then recovered by the second recovery container 720 through the second recovery pathway 710 of the second extraction pathway 700. In this process, the solvent dissolves mono-ortho PCBs and non-DL-PCBs adsorbed to the second adsorption layer 250, and is recovered by the second recovery container 720 as a solution containing the extracted PCBs, namely, as a first analytical sample.

In this step, the second adsorption layer 250 can be heated. When the second adsorption layer 250 is heated, it is possible to extract mono-ortho PCBs and non-DL-PCBs from the second adsorption layer 250 with a smaller amount of solvent. Typically, the heating temperature of the second adsorption layer 250 is preferably controlled up to 95° C.

In the next step for preparing an analytical sample, after stopping the second pump 542, the third valve 631 is switched so that the first ventilation pathway 630 and the open channel 632 communicate with each other in the first extraction pathway 600, and the fourth valve 731 of the second extraction pathway 700 is switched into the closed state. Then, in the solvent outflow pathway 500, the second pump 542 is actuated while the second valve 520 is kept so that the flow channel 510 communicates with the second solvent supplying pathway 541. In this manner, an appropriate amount of solvent reserved in the second solvent container 543 is supplied into the tubular body 210 through the opening 212 via the second solvent supplying pathway 541 and the flow channel 510.

The solvent supplied into the tubular body 210 passes through the second adsorption layer 250 and the first adsorption layer 240 in this order, and flows into the first branch channel 215, and then is recovered by the first recovery container 620 through the first recovery pathway 610 of the first extraction pathway 600. In this process, the solvent dissolves the dioxin group including non-ortho PCBs, PCDDs and PCDFs adsorbed to the first adsorption layer 240, and is recovered by the first recovery container 620 as a solution containing the extracted dioxin group, namely, as a second analytical sample.

In this step, the first adsorption layer 240 can be heated. When the first adsorption layer 240 is heated, it is possible to extract the dioxin group including non-ortho PCBs, PCDDs and PCDFs from the first adsorption layer 240 with a smaller amount of solvent. Typically, the heating temperature of the first adsorption layer 240 is preferably set in the range of 80° C. to 95° C., inclusive.

Through the above extracting steps, an analytical sample of mono-ortho PCBs and an analytical sample of non-ortho PCBs, PCDDs and PCDFs are separately obtained.

These two analytical samples prepared in this manner are separately applied to analysis of dioxins. As an analytical method, depending on the kind of solvent used for extracting dioxins from the adsorption layer 230, typically, a gas chromatography method or a bioassay method can be employed. Examples of gas chromatography method include a GC/MS method such as GC-HRMS, GC-MSMS, GC-QMS and ion trap GC/MS, and a GC/ECD method.

In analysis of the analytical sample for mono-ortho PCBs, since this analytical sample contains substantially no dioxin group including non-ortho PCBs, PCDDs and PCDFs, it is possible to quantify mono-ortho PCBs with high accuracy without being influenced by the dioxin group. Further, since this analytical sample contains non-DL-PCBs together with mono-ortho PCBs, it is possible to additionally quantify non-DL-PCBs contained in the solution of dioxins with high accuracy. For example, a food regulation standard in the European Union (EU), COMMISSION REGULATION (EU) No 1259/2011, designates certain non-DL-PCBs (six kinds of PCBs having 3 to 7 chlorine atoms of IUPAC numbers: #28, #52, #101, #138, #153 and #180) as well as dioxins as analysis targets of harmful substances contained in foods including meat such as beef or pork and eggs, and these PCBs can be quantified by analysis of the above sample.

On the other hand, in analysis of the analytical sample for non-ortho PCBs, PCDDs and PCDFs, which contains substantially no mono-ortho PCBs and non-DL-PCBs, it is possible to quantify non-ortho PCBs, PCDDs and PCDFs with high accuracy without being influenced by mono-ortho PCBs and non-DL-PCBs.

As the GC/MS method, GC-TOFMS may be used. In this case, by mixing the two kinds of analytical samples, the analysis of dioxins can be conducted at one time.

Figure 2:
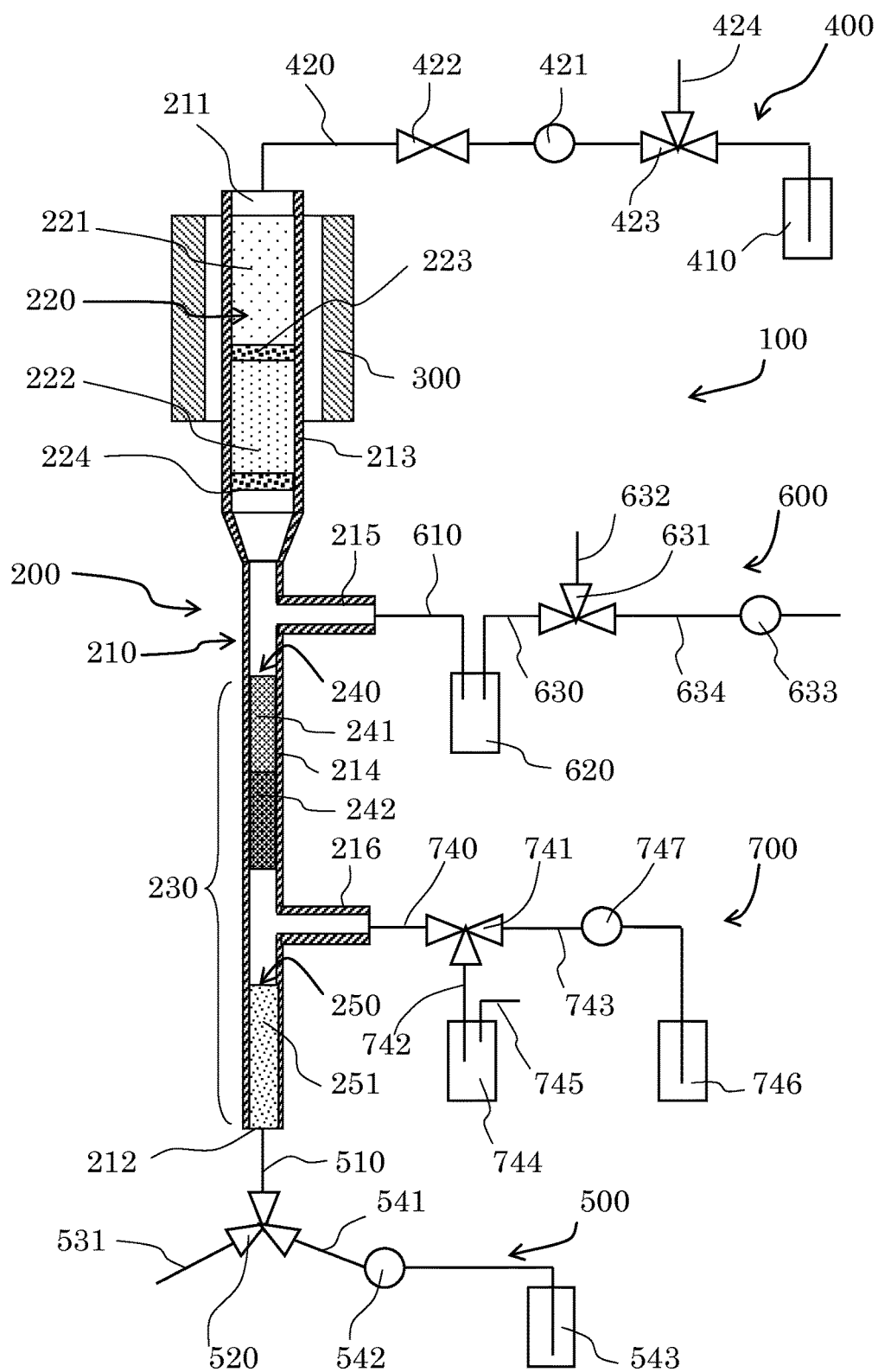
FIG. 2 A partial section view of an outline of a modified example of the apparatus shown in FIG. 1.

In the preparation device 100, the second extraction pathway 700 can be modified as illustrated in FIG. 2. The modified second extraction pathway 700 has a solvent pathway 740 extending from the second branch channel 216. The solvent pathway 740 airtightly communicates with the second branch channel 216 at its one end, and has a fourth valve 741 at its other end. The fourth valve 741 is a three way valve, to which a solvent recovery pathway 742 and a third solvent supply pathway 743 communicate, and is provided for switching the solvent pathway 740 to communicate with either one of the solvent recovery pathway 742 and the third solvent supply pathway 743.

The solvent recovery pathway 742 communicates with a second recovery container 744 for recovering a solvent. The second recovery container 744 has a vent pipe 745 that connects its inside to the outside. The third solvent supply pathway 743 communicates with a third solvent container 746, and has a third pump 747 for sending out a solvent reserved in the third solvent container 746.

In this modified example, the second solvent container 543 reserves a solvent capable of extracting dioxins (mono-ortho PCBs and non-DL-PCBs) adsorbed to the second adsorption layer 250, and the third solvent container 746 reserves a solvent capable of extracting dioxins (non-ortho PCBs, PCDDs and PCDFs) adsorbed to the first adsorption layer 240. The respective solvents reserved in the containers 543 and 746 can be selected according to the analytical method for dioxins.

Specifically, when a gas chromatography method is employed as the analytical method, as the solvent reserved in the third solvent container 746, for example, toluene or benzene can be used. Also, a mixed solvent obtained by adding an aliphatic hydrocarbon solvent or an organic chlorine solvent to toluene or benzene can be used. When the mixed solvent is used, the proportion of toluene or benzene is set at 50% by weight or higher. Examples of the aliphatic hydrocarbon solvent used in the mixed solvent include n-pentane, n-hexane, n-heptane, n-octane, isooctane and cyclohexane. Examples of the organic chlorine solvent include dichloromethane, trichloromethane and tetrachloromethane. Among these extraction solvents, toluene is particularly preferred because dioxins can be extracted with the use of a small amount thereof. On the other hand, as the solvent reserved in the second solvent container 543, besides those reserved in the third solvent container 746, organic chlorine solvents, mixed solvents of an organic chlorine solvent and an aliphatic hydrocarbon solvent and mixed solvents obtained by adding a small amount of toluene to an aliphatic hydrocarbon solvent can be used.

When a bioassay method is employed as the analytical method, as the solvents reserved in the second solvent container 543 and the third solvent container 746, hydrophilic solvents such as dimethyl sulfoxide (DMSO) and methanol can be used.

In the preparation method for an analytical sample for dioxins using the preparation device 100 in which the second extraction pathway 700 is modified, the fourth valve 741 is set so that the solvent pathway 740 communicates with the third solvent supply pathway 743 in an initial state. Next, after conducting the fractionating step of dioxins as described above, an extracting step of dioxins is conducted.

In the extracting step of dioxins, after subjecting each layer of the purification layer 220 and the adsorption layer 230 to a drying treatment as mentioned previously, the compressor 633 is stopped, and in the second extraction pathway 700, the fourth valve 741 is switched so that the solvent pathway 740 communicates with the solvent recovery pathway 742. Also in the solvent outflow pathway 500, the second valve 520 is switched so that the flow channel 510 communicates with the second solvent supplying pathway 541, and the second pump 542 is actuated. In this manner, an appropriate amount of solvent reserved in the second solvent container 543 is supplied into the tubular body 210 through the opening 212 via the second solvent supplying pathway 541 and the flow channel 510.

The solvent supplied into the tubular body 210 passes through the second adsorption layer 250 and flows into the second branch channel 216, and is recovered by the second recovery container 744 through the solvent pathway 740 of the second extraction pathway 700. In this process, the solvent dissolves mono-ortho PCBs and non-DL-PCBs adsorbed to the second adsorption layer 250, and is recovered by the second recovery container 744 as a solution of these PCBs, namely, as a first analytical sample.

In the next step for preparing an analytical sample, after stopping the second pump 542, the third valve 631 is switched so that the first ventilation pathway 630 and the open channel 632 communicate with each other in the first extraction pathway 600, and the fourth valve 741 is switched so that the solvent pathway 740 communicates with the third solvent supply pathway 743 in the second extraction pathway 700. Then, the third pump 747 is actuated to supply an appropriate amount of solvent reserved in the third solvent container 746 from the second branch channel 216 into the tubular body 210 through the third solvent supply channel 743 and the solvent pathway 740.

The solvent supplied into the tubular body 210 passes through the first adsorption layer 240 and flows into the first branch channel 215, and is recovered by the first recovery container 620 through the first recovery pathway 610 of the first extraction pathway 600. In this process, the solvent dissolves the dioxin group including non-ortho PCBs, PCDDs and PCDFs adsorbed to the first adsorption layer 240, and is recovered by the first recovery container 620 as a solution of the dioxin group, namely as a second analytical sample. The second analytical sample is prepared without passage of the solvent through the second adsorption layer 250, and is highly fractionated from mono-ortho PCBs and non-DL-PCBs.

The first analytical sample and the second analytical sample obtained are applied to analysis for dioxins as mentioned previously.

In the preparation device 100 in which the second extraction pathway 700 is modified as illustrated in FIG. 2, the order of extraction of a dioxin group including non-ortho PCBs, PCDDs and PCDFs from the first adsorption layer 240, and extraction of mono-ortho PCBs and non-DL-PCBs from the second adsorption layer 250 may be reversed in the extracting step of dioxins. That is, after extracting a dioxin group including non-ortho PCBs, PCDDs and PCDFs from the first adsorption layer 240 first, mono-ortho PCBs and non-DL-PCBs may be extracted from the second adsorption layer 250.

Second Embodiment

Figure 3:
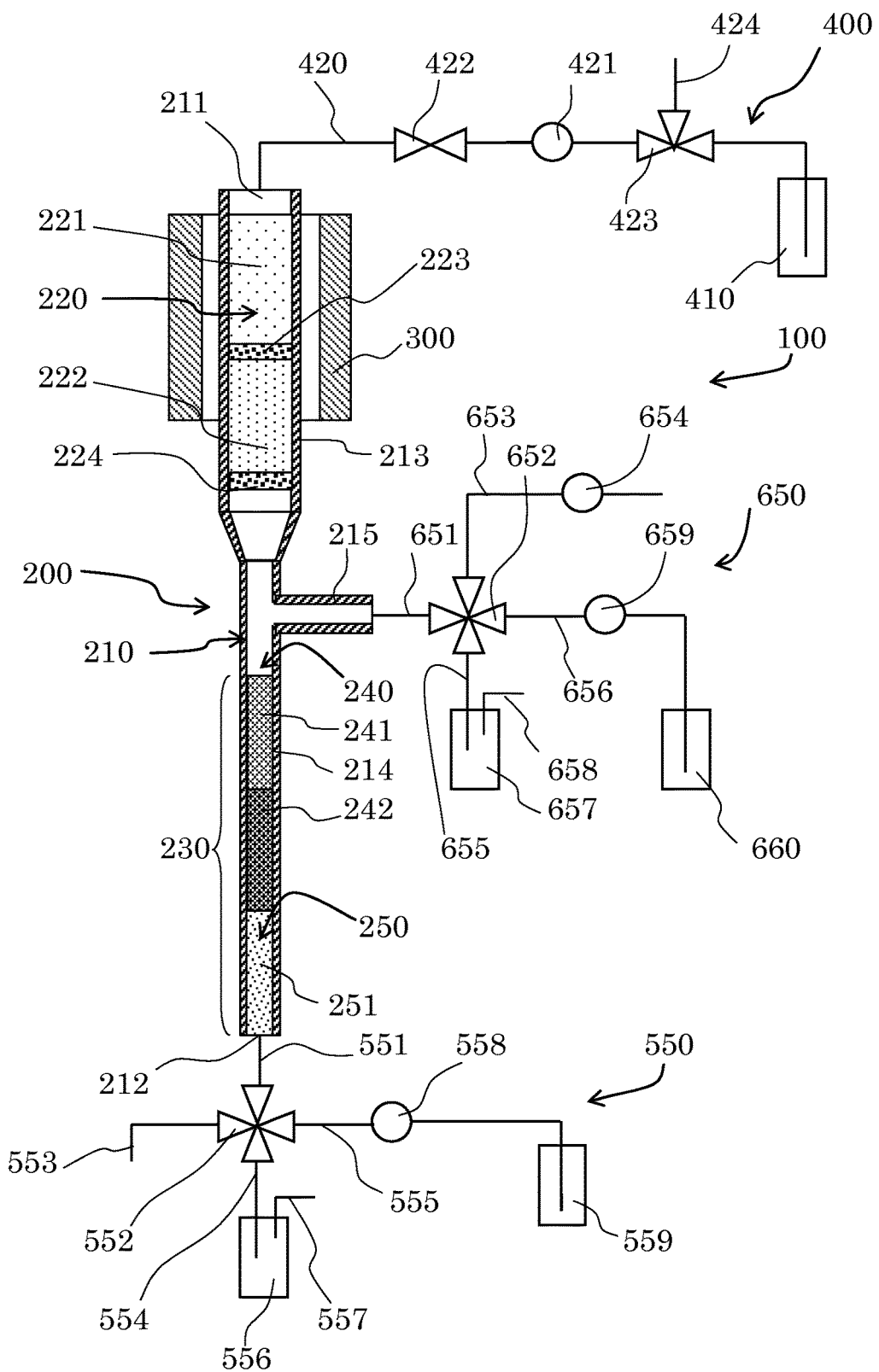
FIG. 3 A partial section view of an outline of a second example of an apparatus for conducting a method for preparing an analytical sample according to the present invention.

Referring to FIG. 3, the second example of an apparatus capable of conducting a method for preparing an analytical sample according to the present invention will be described. In FIG. 3, a preparation device 100 is capable of preparing an analytical sample suited for analysis by a gas chromatography method, and mainly includes a fractionating tool 200, a heating device 300, a solvent supplying device 400, a solvent outflow pathway 550 and an extraction pathway 650.

The fractionating tool 200 differs from the fractionating tool 200 described in the first embodiment in structures of a small-diameter portion 214 and an adsorption layer 230 of a tubular body 210. Specifically, the small-diameter portion 214 has a first branch channel 215 only as a branch channel. In the adsorption layer 230, a first adsorption layer 240 and a second adsorption layer 250 are in close contact with each other. Therefore, the length of the small-diameter portion 214 is shorter than that of the fractionating tool 200 described in the first embodiment.

The heating device 300 and the solvent supplying device 400 are as described in the first embodiment.

The solvent outflow pathway 550 has a flow channel 551 airtightly connected to an opening 212 of the tubular body 210. The flow channel 551 has a second valve 552. The second valve 552 is a four way valve, to which a disposal pathway 553 for disposing of a solvent from the tubular body 210, a recovery pathway 554 for recovering a solvent from the tubular body 210 and a supply pathway 555 for supplying the tubular body 210 with a solvent communicate, and is provided for switching the flow channel 551 to communicate with either one of the disposal pathway 553, the recovery pathway 554 and the supply pathway 555.

The recovery pathway 554 has a recovery container 556 for a solvent. The recovery container 556 has a vent pipe 557 that connects its inside to the outside. The supply pathway 555 has a second pump 558, and communicates with a second solvent container 559 for reserving an extraction solvent of dioxins trapped by the fractionating tool 200.

The extraction solvent reserved in the second solvent container 559 is capable of dissolving dioxins, and can be toluene or benzene. Also, a mixed solvent obtained, for example, by adding an aliphatic hydrocarbon solvent or an organic chlorine solvent to toluene or benzene can be used. When the mixed solvent is used, the proportion of toluene or benzene is set at 50% by weight or higher. Examples of the aliphatic hydrocarbon solvent used in the mixed solvent include n-pentane, n-hexane, n-heptane, n-octane, isooctane and cyclohexane. Examples of the organic chlorine solvent include dichloromethane, trichloromethane and tetrachloromethane. Among these extraction solvents, toluene is particularly preferred because dioxins can be extracted from the fractionating tool 200 with the use of a small amount thereof.

The extraction pathway 650 has a solvent pathway 651 extending from the first branch channel 215. The solvent pathway 651 airtightly communicates with the first branch channel 215 at its one end, and has a third valve 652 at its other end. The third valve 652 is a four way valve, to which an air supply pathway 653 having a compressor 654 for sending compressed air, a recovery pathway 655 for recovering a solvent from the first branch channel 215, and a supply pathway 656 for supplying the tubular body 210 with a solvent communicate, and is provided for switching the solvent pathway 651 to communicate with either one of the air supply pathway 653, the recovery pathway 655 and the supply pathway 656.

The recovery pathway 655 has a recovery container 657 for recovering a solvent. The recovery container 657 has a vent pipe 658 that connects its inside to the outside. The supply pathway 656 has a third pump 659, and communicates with a third solvent container 660 for reserving an extraction solvent of dioxins trapped by the fractionating tool 200.

The extraction solvent reserved in the third solvent container 660 substantially does not dissolve a dioxin group including non-ortho PCBs, PCDDs and PCDFs, but well dissolves mono-ortho PCBs and non-DL-PCBs, and is, for example, an organic chlorine solvent, a mixed solvent obtainable by adding an aliphatic hydrocarbon solvent to an organic chlorine solvent, a mixed solvent obtainable by adding toluene to an aliphatic hydrocarbon solvent (content of toluene is typically about 10 to 15% by weight) or the like. Examples of the organic chlorine solvent used herein include dichloromethane, trichloromethane and tetrachloromethane. Examples of the aliphatic hydrocarbon solvent include n-pentane, n-hexane, n-heptane, n-octane, isooctane and cyclohexane.

Next, a preparation method of an analytical sample of dioxins using the above-described preparation device 100 will be described. First, in the preparation device 100, the first valve 422, the air introducing valve 423, the second valve 552 and the third valve 652 are set at predetermined initial states. To be more specific, the first valve 422 is set to be in the open state, and the air introducing valve 423 is set to communicate with the side of the first solvent container 410. The second valve 552 is set so that the flow channel 551 communicates with the disposal pathway 553. Further, the third valve 652 is set so that the solvent pathway 651 communicates with the air supply pathway 653.

Next, after conducting the separating step of dioxins in the same manner as in the first embodiment, each layer of the purification layer 220 and the adsorption layer 230 is subjected to a drying treatment, and an extracting step of dioxins is conducted. A drying treatment of the purification layer 220 can be conducted in the same manner as in the first embodiment. In the subsequent drying treatment of the adsorption layer 230, the first valve 422 of the solvent supplying device 400 is switched to the closed state. Then, in the extraction pathway 650, the compressor 654 is actuated.

By operation of the compressor 654, compressed air is supplied to the first branch channel 215 through the air supply pathway 653 and the solvent pathway 651. The compressed air passes through the adsorption layer 230, and flows into the flow channel 551 through the opening 212, and is then discharged through the disposal pathway 553. In this process, the solvent remaining in each layer of the adsorption layer 230 is pushed out by the compressed air, and is discharged from the disposal pathway 553 together with the compressed air. As a result, each layer of the adsorption layer 230 undergoes a drying treatment.

In an extracting step of dioxins, first, in the solvent outflow pathway 550, the second valve 552 is switched so that the flow channel 551 communicates with the recovery pathway 554. Also, in the extraction pathway 650, the third valve 652 is switched so that the solvent pathway 651 communicates with the supply pathway 656, and the third pump 659 is actuated. In this manner, an appropriate amount of solvent reserved in the third solvent container 660 is supplied into the tubular body 210 from the first branch channel 215 through the supply pathway 656 and the solvent pathway 651.

The solvent supplied into the tubular body 210 passes through the adsorption layer 230, flows into the flow channel 551 and the recovery pathway 554 through the opening 212, and is recovered by the recovery container 556. In this process, the solvent dissolves and extracts mono-ortho PCBs and non-DL-PCBs adsorbed to the second adsorption layer 250, and is recovered by the recovery container 556 as a solution of these PCBs, namely as a first analytical sample.

In the next step for extracting dioxins, the third pump 659 is stopped, and in the extraction pathway 650, the third valve 652 is switched so that the solvent pathway 651 communicates with the recovery pathway 655. Then, in the solvent outflow pathway 550, the second valve 552 is switched so that the flow channel 551 communicates with the supply channel 555, and the second pump 558 is actuated. In this manner, an appropriate amount of solvent reserved in the second solvent container 559 is supplied into the tubular body 210 through the opening 212 via the supply channel 555 and the flow channel 551.

The solvent supplied into the tubular body 210 passes through the second adsorption layer 250 and the first adsorption layer 240 in this order and flows into the first branch channel 215, and is recovered by the recovery container 657 through the solvent pathway 651 and the recovery pathway 655 of the extraction pathway 650. In this process, the solvent dissolves and extracts a dioxin group including non-ortho PCBs, PCDDs and PCDFs adsorbed to the first adsorption layer 240, and is recovered by the recovery container 657 as a solution of this dioxin group, namely as a second analytical sample.

Through the above steps, an analytical sample for mono-ortho PCBs and an analytical sample for non-ortho PCBs, PCDDs and PCDFs are separately obtained, and each analytical sample is applied to analysis by a gas chromatography method.

Third Embodiment

Figure 4:
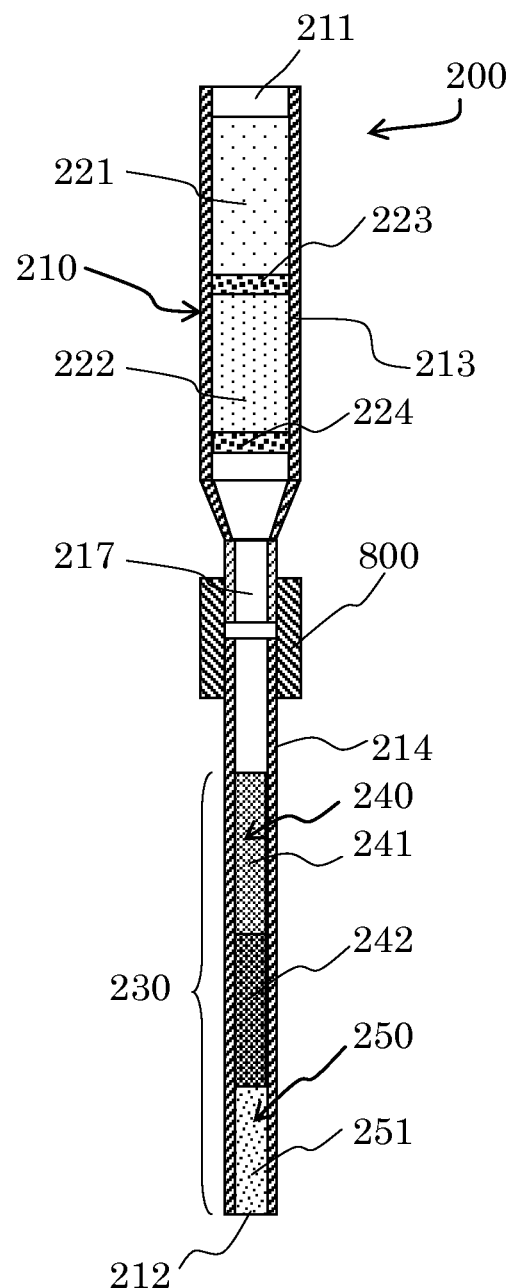
FIG. 4 A section view showing an outline of one example of a fractionating tool for conducting a method for preparing an analytical sample according to the present invention.

Referring to FIG. 4, another example of the fractionating tool capable of conducting a method for preparing an analytical sample according to the present invention will be described. In the drawing, likewise the fractionating tool 200 used in the preparation apparatus 100 of the second embodiment, a fractionating tool 200 has a tubular body 210 having a large-diameter portion 213 and a small-diameter portion 214. However, the fractionating tool 200 of this example is separated into the large-diameter portion 213 and the small-diameter portion 214, and forms the integrated tubular body 210 by means of a connecting tool 800 separably joining the large-diameter portion 213 with the small-diameter portion 214.

The large-diameter portion 213 is formed into a cylinder opening at both ends, and has a neck portion 217 having the same outer diameter and inner diameter as those of the small-diameter portion 214 in the end part on the side of a sulfuric acid silica gel layer 222. The small-diameter portion 214 is formed into a cylinder opening at both ends, and in an adsorption layer 230, a first adsorption layer 240 and a second adsorption layer 250 are in close contact with each other. The connecting tool 800 is formed into a cylinder that is formed by using, for example, resin materials or other materials having resistance to various organic solvents, in particular, hydrocarbon solvents. By inserting the neck portion 217 of the large-diameter portion 213 and the end part of the small-diameter portion 214 on the side of the first adsorption layer 240 in the connecting tool 800, the large-diameter portion 213 and the small-diameter portion 214 are connected in a liquid-tight manner.

In preparing an analytical sample for dioxins using the preparation apparatus 100 of this example, the fractionating step for dioxins is executed in a similar manner to the first embodiment in the condition that the large-diameter portion 213 and the small-diameter portion 214 are connected with each other in the fractionating tool 200. This fractionating step may be executed manually. After drying the purification layer 220 and the adsorption layer 230 subsequent to the fractionating step, the small-diameter portion 214 is separated from the connecting tool 800.

In extraction of dioxins from the adsorption layer 230, similarly to the case of the second embodiment, by supplying a solvent that substantially does not dissolve a dioxin group including non-ortho PCBs, PCDDs and PCDFs, but well dissolves mono-ortho PCBs and non-DL-PCBs from the end part on the side of the first adsorption layer 240 of the small-diameter portion 214, mono-ortho PCBs and non-DL-PCBs adsorbed to the second adsorption layer 250 are extracted to obtain a first analytical sample. Thereafter, by supplying a solvent capable of dissolving dioxins from the end part (opening 212) of the small-diameter portion 214 on the side of the second adsorption layer 250, the dioxin group including non-ortho PCBs, PCDDs and PCDFs adsorbed to the first adsorption layer 240 is extracted to obtain a second analytical sample.

Such an extraction operation may be conducted manually or mechanically.

Figure 5:
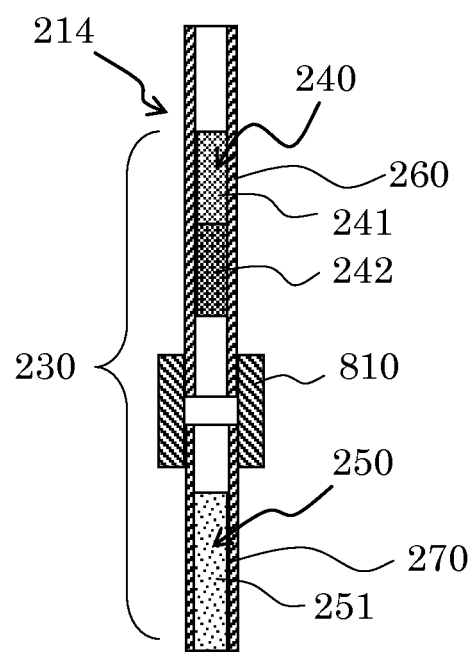
FIG. 5 A section view showing an outline of part of a modified example of the fractionating tool shown in FIG. 4.

Part of a modified example of the fractionating tool 200 of the present embodiment is shown in FIG. 5. The small-diameter portion 214 of the fractionating tool 200 according to this modified example is separated into a first part 260 packed with the first adsorption layer 240 and a second part 270 packed with the second adsorption layer 250, and the first part 260 and the second part 270 are integrated by being detachably connected with each other by means of a connecting tool 810. The connecting tool 810 is similar to the connecting tool 800 for connecting the large-diameter portion 213 with the small-diameter portion 214.

The fractionating tool 200 of this modified example makes it possible to separate the small-diameter portion 214 from the large-diameter portion 213, and further to separate the small-diameter portion 214 into the first part 260 and the second part 270. Therefore, in extracting dioxins from the adsorption layer 230, it is possible to conduct an extraction operation for dioxins separately for the first adsorption layer 240 of the first part 260 and the second adsorption layer 250 of the second part 270, and to fractionate the analytical sample of mono-ortho PCBs and non-DL-PCBs, and the analytical sample of a dioxin group including non-ortho PCBs, PCDDs and PCDFs more accurately.

Examples of Other Embodiments (1) In the fractionating tool 200 according to each embodiment as described above, the silver nitrate silica gel layer 221 is arranged to be situated on the side of the opening 211 in the purification layer 220, however, the order of the silver nitrate silica gel layer 221 and the sulfuric acid silica gel layer 222 may be reversed.

However, when the silver nitrate silica gel layer 221 and the sulfuric acid silica gel layer 222 are reversed, non-DL-PCBs having a small number of chlorine atoms react with the sulfuric acid silica gel layer 222, so that the recovery rate of non-DL-PCBs having a small number of chlorine atoms in the analytical sample can be decreased. Therefore, in the case where non-DL-PCBs, in particular, non-DL-PCBs having a small number of chlorine atoms must be analyzed together with dioxins (for example, in the case where dioxins in foods are analyzed according to the food regulation standard in EU), it is preferred to arrange the silver nitrate silica gel layer 221 on the side of the opening 211 in the purification layer 220.

(2) In the purification layer 220 of the fractionating tool 200 according to each embodiment as described above, the first active silica gel layer 223 and the second active silica gel layer 224 may be omitted.

(3) The large-diameter portion 213 of the fractionating tool 200 may be separated into the part packed with the silver nitrate silica gel layer 221 and the part packed with the sulfuric acid silica gel layer 222, and these parts may be connected before use. This structure can make it possible to increase the recovery rate of dioxins.

(4) In preparation method of an analytical sample of dioxins according to each embodiment as described above, the purification layer 220 is heated by the heating device 300, however, each preparation method can be practiced in a similar manner even when the purification layer 220 is not heated.

(5) In preparation method of an analytical sample of dioxins according to each embodiment as described above, the drying treatment of the purification layer 220 and the adsorption layer 230 can be appropriately changed by either one of the method by aspiration of the air, and supply of compressed air by a compressor. Also, the purification layer 220 and the adsorption layer 230 may be dried by supply of nitrogen gas. Further, the drying treatment of the purification layer 220 and the adsorption layer 230 may be omitted.

EXAMPLES

Hereinafter, the present invention will be concretely described by way of examples, however, the present invention is not limited by these examples.

In the following examples, the following fish oil sample or liquid paraffin sample was used as a solution of dioxins.

Fish Oil Sample:

Fish oil (trade name "Fish oil, from menhaden" available from Sigma Aldrich) which was confirmed by the method described in Japanese Industrial Standards JIS K 0311 (2005) that it contains substantially no dioxins, and to which dioxins standard substance (trade name "DF-LCS-A", available from Wellington Laboratories) and PCBs standard substance (trade name "PCB-LCS-A1" available from Wellington Laboratories) are added was used. The fish oil contains a trace amount of PCDE as impurities. The dioxins standard substance contains PCDDs, PCDFs and DL-PCBs, all labeled with $^{13}C_{12}$. The PCBs standard substance includes the following eight kinds of non-DL-PCBs (in parentheses are IUPAC numbers) having 1 to 8 chlorine atoms and labeled with $^{13}C_{12}$.

$^{13}C_{12}$-4-MoCB (#3)
$^{13}C_{12}$-4,4'-DiCB (#15)
$^{13}C_{12}$-2,4,4'-TrCB (#28)
$^{13}C_{12}$-2,2',5,5'-TeCB (#52)
$^{13}C_{12}$-2,3',4,4',5-PeCB (#118)
$^{13}C_{12}$-2,2',4,4',5,5'-HxCB (#153)
$^{13}C_{12}$-2,2',3,4,4',5,5'-HpCB (#180)
$^{13}C_{12}$-2,2',3,3',4,4',5,5'-OcCB (#194)

Among six kinds of PCBs isomers #28, #52, #101, #138, #153 and #180 (PCBs isomers having 3 to 7 chlorine atoms) which are targets of the food regulation in EU, the above eight kinds of non-DL-PCBs include four kinds of isomers #28, #52, #153 and #180 only, and do not include two kinds of isomers #101 (number of chlorine atoms: 5) and #138 (number of chlorine atoms: 6). However, the above eight kinds of non-DL-PCBs substantially include all the six kinds of the EU food regulation target PCBs because the EU food regulation allows measuring different isomers having the corresponding number of chlorine atoms in place of the target isomers, and accordingly the above eight kinds of non-DL-PCBs include #118 and #153 respectively having the same number of chlorine atoms as #101 and #138.

Liquid Paraffin Sample:

Liquid paraffin (available from Kanto Chemical Co., Inc.) which was confirmed by the method described in Japanese Industrial Standards JIS K 0311 (2005) that it is substantially free from dioxins, and to which the dioxins standard substance and the PCBs standard substance same as those used in preparation of the fish oil sample are added was added.

In the following examples, fillers of layers packed in the fractionating tool are as follows.

Silver Nitrate Silica Gel Layer:

Silver nitrate silica gel prepared by adding the whole amount of an aqueous solution of 11.2 g of silver nitrate (available from Wako Pure Chemical Industries, Ltd.) dissolved in 30 mL of distilled water to 100 g of active silica gel (available from Kanto Chemical Co., Inc.), uniformly mixing the aqueous solution and the active silica gel, and then drying the resultant active silica gel by heating to 70° C. under reduced pressure by using a rotary evaporator was used.

Sulfuric Acid Silica Gel Layer:

Sulfuric acid silica gel prepared by uniformly adding 78.7 g of concentrated sulfuric acid (available from Wako Pure Chemical Industries, Ltd.) to 100 g of active silica gel (available from Kanto Chemical Co., Inc.) and then drying the resultant active silica gel was used.

Activated Carbon-Containing Silica Gel Layer:

Activated carbon-containing silica gel obtained by adding activated carbon (trade name "KURARAY COAL PK-DN" available from Kuraray Chemical Co., Ltd.) to active silica gel (available from Kanto Chemical Co., Inc.) and uniformly mixing the activated carbon and the active silica gel was used.

Graphite-Containing Silica Gel Layer:

Graphite-containing silica gel obtained by adding graphite (trade name "ENVI-Carb" available from Sigma-Aldrich) to active silica gel (available from Kanto Chemical Co., Inc.) and uniformly mixing the graphite and the active silica gel was used.

Activated Carbon Layer:

Activated carbon (trade name "KURARAY COAL PK-DN" available from Kuraray Chemical Co., Ltd.) was used.

Graphite Layer:

Graphite (trade name "ENVI-Carb" available from Sigma-Aldrich) was used.

Alumina Layer:

Trade name "Aluminium Oxide 90 active basic—(activity stage I) for column chromatography" (particle size: 0.063 to 0.200 mm) available from Merck was used.

Examples 1 to 6

Using the preparation device for an analytical sample for dioxins shown in FIG. 1, dioxins contained in the fish oil sample were extracted. The specification of the fractionating tool used in the preparation device is as follows.

Purification Layer:

In a large-diameter portion of a tubular body having an outer diameter of 18.5 mm, an inner diameter of 12.5 mm, and a length of 200 mm, as shown in FIG. 1, 4.4 g (packing height: 60 mm) of silver nitrate silica gel was stacked on 8.5 g (packing height: 80 mm) of sulfuric acid silica gel to form this layer (stacking of the first active silica gel layer and the second active silica gel layer was omitted).

Adsorption Layer:

In a small-diameter portion of a tubular body having an outer diameter of 8 mm, an inner diameter of 6 mm, and a length of 30 mm, as shown in FIG. 1, 0.06 g (packing height: 5 mm) of activated carbon-containing silica gel which is an upper layer was stacked and packed on 0.22 g (packing height: 25 mm) of graphite-containing silica gel which is a lower layer to form this layer. In the small-diameter portion, packing of alumina was omitted. The proportion of activated carbon contained in the activated carbon-containing silica gel, the proportion of graphite contained in the graphite-containing silica gel, and the stacking ratio (volume ratio) between the activated carbon-containing silica gel layer and the graphite-containing silica gel layer are shown in Table 1.

TABLE 1

| Example | Proportion of activated carbon (*1) (% by weight) | Proportion of graphite (*2) (% by weight) | Volume ratio (*3) |
|---|---|---|---|
| 1 | 0.13 | 25 | 1:1 |
| 2 | 0.13 | 25 | 1:5 |
| 3 | 0.13 | 25 | 1:9 |
| 4 | 0.13 | 25 | 1:12 |
| 5 | 0.013 | 25 | 1:5 |
| 6 | 5.0 | 25 | 1:5 |

(*1) Proportion of activated carbon contained in activated carbon-containing silica gel
(*2) Proportion of graphite contained in graphite-containing silica gel
(*3) Volume ratio (A:B) between activated carbon-containing silica gel layer (A) and graphite-containing silica gel layer (B)

In the extraction operation of dioxins, about 4 mL of the fish oil sample solution was added to the silver nitrate silica gel layer of the purification layer, and the purification layer was heated to 60° C. Then, the purification layer was gradually supplied with 85 mL of n-hexane, and the supplied n-hexane was allowed to pass through the purification layer and the adsorption layer. After n-hexane had passed through the adsorption layer, the adsorption layer was treated to be dried by allowing compressed air to pass therethrough. Then, after heating the adsorption layer to 90° C., 1.5 mL of toluene was supplied from the lower layer side of the adsorption layer, and toluene having passed through the adsorption layer was recovered through the first branch channel.

Dioxins contained in the recovered toluene were quantitatively analyzed by the HRGC/HRMS method. The calculation results of recovery rates of dioxins are shown in Table 2. The term "recovery rate of dioxins" means the proportion (%) of the amount of dioxins contained in the solvent having extracted dioxins, to the initial amount of dioxins added to the sample.

TABLE 2

| | | Recovery rate (%) Example | | | | | |
|---|---|---|---|---|---|---|---|
| | | 1 | 2 | 3 | 4 | 5 | 6 |
| PCDDs | $^{13}C_{12}$-2,3,7,8-TeCDD | 97 | 93 | 100 | 108 | 94 | 85 |
| | $^{13}C_{12}$-1,2,3,7,8-PeCDD | 94 | 95 | 102 | 104 | 91 | 88 |
| | $^{13}C_{12}$-1,2,3,4,7,8-HxCDD | 99 | 95 | 97 | 93 | 87 | 91 |
| | $^{13}C_{12}$-1,2,3,6,7,8-HxCDD | 99 | 98 | 94 | 87 | 84 | 92 |
| | $^{13}C_{12}$-1,2,3,7,8,9-HxCDD | 101 | 95 | 97 | 94 | 91 | 83 |
| | $^{13}C_{12}$-1,2,3,4,6,7,8-HpCDD | 99 | 91 | 92 | 75 | 79 | 77 |
| | $^{13}C_{12}$-OCDD | 88 | 82 | 73 | 50 | 64 | 60 |
| PCDFs | $^{13}C_{12}$-2,3,7,8-TeCDF | 101 | 99 | 102 | 105 | 97 | 88 |
| | $^{13}C_{12}$-1,2,3,7,8-PeCDF | 98 | 95 | 101 | 102 | 93 | 89 |
| | $^{13}C_{12}$-2,3,4,7,8-PeCDF | 94 | 97 | 98 | 100 | 88 | 90 |
| | $^{13}C_{12}$-1,2,3,4,7,8-HxCDF | 95 | 100 | 93 | 86 | 84 | 91 |
| | $^{13}C_{12}$-1,2,3,6,7,8-HxCDF | 94 | 94 | 92 | 94 | 85 | 89 |
| | $^{13}C_{12}$-1,2,3,7,8,9-HxCDF | 94 | 101 | 97 | 104 | 90 | 92 |
| | $^{13}C_{12}$-2,3,4,6,7,8-HxCDF | 97 | 98 | 94 | 80 | 85 | 88 |
| | $^{13}C_{12}$-1,2,3,4,6,7,8-HpCDF | 96 | 90 | 81 | 69 | 66 | 72 |
| | $^{13}C_{12}$-1,2,3,4,7,8,9-HpCDF | 95 | 93 | 98 | 82 | 84 | 87 |
| | $^{13}C_{12}$-OCDF | 90 | 83 | 79 | 53 | 65 | 65 |
| Non-ortho PCBs | $^{13}C_{12}$-3,4,4',5-TeCB (#81) | 114 | 101 | 99 | 114 | 96 | 95 |
| | $^{13}C_{12}$-3,3',4,4'-TeCB (#77) | 115 | 101 | 98 | 115 | 94 | 94 |
| | $^{13}C_{12}$-3,3',4,4',5-PeCB (#126) | 115 | 95 | 105 | 115 | 104 | 104 |
| | $^{13}C_{12}$-3,3',4,4',5,5'-HxCB (#169) | 119 | 107 | 110 | 119 | 99 | 99 |
| Mono-ortho PCBs | $^{13}C_{12}$-2',3,4,4',5-PeCB (#123) | 1 | 1 | 1 | 2 | 1 | 0 |
| | $^{13}C_{12}$-2,3',4,4',5-PeCB (#118) | 4 | 1 | 1 | 5 | 1 | 1 |
| | $^{13}C_{12}$-2,3,3',4,4'-PeCB (#105) | 2 | 1 | 2 | 2 | 1 | 1 |
| | $^{13}C_{12}$-2,3,4,4',5-PeCB (#114) | 1 | 0 | 0 | 0 | 0 | 0 |
| | $^{13}C_{12}$-2,3',4,4',5,5'-HxCB (#167) | 1 | 2 | 0 | 0 | 0 | 0 |
| | $^{13}C_{12}$-2,3,3',4,4',5-HxCB (#156) | 1 | 1 | 0 | 2 | 0 | 0 |
| | $^{13}C_{12}$-2,3,3',4,4',5'-HxCB (#157) | 2 | 1 | 1 | 3 | 1 | 0 |
| | $^{13}C_{12}$-2,3,3',4,4',5,5'-HpCB (#189) | 1 | 1 | 0 | 2 | 0 | 0 |

According to Table 2, the recovered toluene contains PCDDs, PCDFs and non-ortho PCBs at high recovery rates, specifically at the rate of 50% or higher which is the standard required in various regulations for dioxins, and is substantially free from mono-ortho PCBs. The results demonstrate that in Examples 1 to 6, a dioxin group including non-ortho PCBs, PCDDs and PCDFs was separated from mono-ortho PCBs at high accuracy.

Since no substantial interference peak by PCDE was observed in the quantification by the HRGC/HRMS method, it was revealed that in Examples 1 to 6, a dioxin group including non-ortho PCBs, PCDDs and PCDFs was separated effectively from PCDE.

Comparative Examples 1 to 5

The specifications of the adsorption layer of the fractionating tool only were modified in the preparation device for an analytical sample for dioxins, and dioxins contained in the fish oil sample was extracted in the same manner as in Examples 1 to 6. Then, the extract was quantitatively analyzed by the HRGC/HRMS method, and the recovery rate of dioxins was calculated. The specifications of the adsorption layer are as shown in Table 3. The results are shown in Table 4.

TABLE 3

| | Adsorption layer | | | | | | |
|---|---|---|---|---|---|---|---|
| | Upper layer | | | Lower layer | | | Volume ratio |
| Comparative Example | Material | Packing amount (g) | Packing height (mm) | Material | Packing amount (g) | Packing height (mm) | between upper layer and lower |
| 1 | Activated carbon-containing silica gel (*1) | 0.40 | 30 | None | — | — | — |
| 2 | Graphite | 0.32 | 30 | None | — | — | — |
| 3 | Graphite | 0.050 | 5 | Activated carbon-containing silica gel (*1) | 0.33 | 25 | 1:5 |
| 4 | Activated carbon-containing silica gel (*1) | 0.055 | 5 | Graphite | 0.25 | 25 | 1:5 |

TABLE 3-continued

| Comparative Example | Adsorption layer | | | | | | Volume ratio between upper layer and lower |
|---|---|---|---|---|---|---|---|
| | Upper layer | | | Lower layer | | | |
| | Material | Packing amount (g) | Packing height (mm) | Material | Packing amount (g) | Packing height (mm) | |
| 5 | Graphite-containing silica gel (*2) | 0.050 | 5 | Activated carbon-containing silica gel (*1) | 0.33 | 25 | 1:5 |

(*1): Proportion of activated carbon contained in activated carbon-containing silica gel: 0.13% by weight
(*2): Proportion of graphite contained in graphite-containing silica gel: 50% by weight
*3: Volume ratio (A:B) between upper layer (A) and lower layer (B)

TABLE 4

| | | Recovery rate (%) Comparative Example | | | | |
|---|---|---|---|---|---|---|
| | | 1 | 2 | 3 | 4 | 5 |
| PCDDs | $^{13}C_{12}$-2,3,7,8-TeCDD | 95 | 88 | 96 | 100 | 94 |
| | $^{13}C_{12}$-1,2,3,7,8-PeCDD | 116 | 88 | 92 | 101 | 97 |
| | $^{13}C_{12}$-1,2,3,4,7,8-HxCDD | 108 | 65 | 75 | 99 | 86 |
| | $^{13}C_{12}$-1,2,3,6,7,8-HxCDD | 102 | 60 | 67 | 94 | 82 |
| | $^{13}C_{12}$-1,2,3,7,8,9-HxCDD | 104 | 61 | 66 | 95 | 87 |
| | $^{13}C_{12}$-1,2,3,4,6,7,8-HpCDD | 104 | 45 | 52 | 93 | 69 |
| | $^{13}C_{12}$-OCDD | 94 | 26 | 28 | 83 | 47 |
| PCDFs | $^{13}C_{12}$-2,3,7,8-TeCDF | 92 | 91 | 95 | 94 | 91 |
| | $^{13}C_{12}$-1,2,3,7,8-PeCDF | 93 | 84 | 86 | 100 | 89 |
| | $^{13}C_{12}$-2,3,4,7,8-PeCDF | 106 | 90 | 93 | 99 | 90 |
| | $^{13}C_{12}$-1,2,3,4,7,8-HxCDF | 92 | 61 | 69 | 93 | 81 |
| | $^{13}C_{12}$-1,2,3,6,7,8-HxCDF | 92 | 61 | 65 | 93 | 79 |
| | $^{13}C_{12}$-1,2,3,7,8,9-HxCDF | 92 | 68 | 75 | 93 | 93 |
| | $^{13}C_{12}$-2,3,4,6,7,8-HxCDF | 99 | 62 | 67 | 91 | 83 |
| | $^{13}C_{12}$-1,2,3,4,6,7,8-HpCDF | 79 | 38 | 42 | 87 | 60 |
| | $^{13}C_{12}$-1,2,3,4,7,8,9-HpCDF | 97 | 54 | 62 | 94 | 74 |
| | $^{13}C_{12}$-OCDF | 86 | 31 | 36 | 85 | 53 |
| Non-ortho PCBs | $^{13}C_{12}$-3,4,4',5-TeCB (#81) | 69 | 74 | 80 | 80 | 82 |
| | $^{13}C_{12}$-3,3',4,4'-TeCB (#77) | 66 | 70 | 75 | 75 | 76 |
| | $^{13}C_{12}$-3,3',4,4',5-PeCB (#126) | 65 | 72 | 77 | 79 | 81 |
| | $^{13}C_{12}$-3,3',4,4',5,5'-HxCB (#169) | 72 | 72 | 78 | 72 | 83 |
| Mono-ortho PCBs | $^{13}C_{12}$-2',3,4,4',5-PeCB (#123) | 12 | 16 | 9 | 16 | 12 |
| | $^{13}C_{12}$-2,3,4,4',5-PeCB (#118) | 56 | 58 | 22 | 47 | 26 |
| | $^{13}C_{12}$-2,3,3',4,4'-PeCB (#105) | 51 | 68 | 43 | 70 | 48 |
| | $^{13}C_{12}$-2,3,4,4',5-PeCB (#114) | 20 | 0 | 8 | 0 | 8 |
| | $^{13}C_{12}$-2,3',4,4',5,5'-HxCB (#167) | 50 | 56 | 37 | 54 | 35 |
| | $^{13}C_{12}$-2,3,3',4,4',5-HxCB (#156) | 49 | 45 | 37 | 47 | 43 |
| | $^{13}C_{12}$-2,3,3',4,4',5'-HxCB (#157) | 67 | 75 | 58 | 75 | 63 |
| | $^{13}C_{12}$-2,3,3',4,4',5,5'-HpCB (#189) | 61 | 58 | 48 | 61 | 57 |

According to Table 4, in the extract, recovery rates of some of those having a large number of chlorine atoms among PCDDs and PCDFs are low, and a considerable quantity of mono-ortho PCBs are contained. The results demonstrate that in Comparative Examples 1 to 5, it was impossible to separate a dioxin group including non-ortho PCBs, PCDDs and PCDFs from mono-ortho PCBs.

Also, in Comparative Examples 2 to 5, since an interference peak by PCDE was observed in measurement results by the HRGC/HRMS method, it was revealed that PCDE was mixed into the dioxin group including non-ortho PCBs, PCDDs and PCDFs.

Examples 7 to 8

Similarly to Examples 1 to 6, dioxins contained in the liquid paraffin sample were extracted with toluene. In this case, in the adsorption layer, the proportion of activated carbon contained in activated carbon-containing silica gel, the proportion of graphite contained in graphite-containing silica gel, and the stacking ratio (volume ration) between the activated carbon-containing silica gel layer and the graphite-containing silica gel layer were set as shown in Table 5.

TABLE 5

| Example | Proportion of activated carbon (*1) (% by weight) | Proportion of graphite (*2) (% by weight) | Volume ratio (*3) |
|---|---|---|---|
| 7 | 0.13 | 25 | 1:5 |
| 8 | 0.13 | 5 | 1:5 |

(*1): Proportion of activated carbon contained in activated carbon-containing silica gel
(*2): Proportion of graphite contained in graphite-containing silica gel
(*3): Volume ratio (A:B) between activated carbon-containing silica gel layer (A) and graphite-containing silica gel layer (B)

Dioxins contained in the toluene extracts were quantitatively analyzed by the HRGC/HRMS method. The calculation results of recovery rates of dioxins are shown in Table 6. Here, in order to confirm that PCDDs, PCDFs and non-ortho PCBs can be extracted from the adsorption layer without influenced by liquid paraffin, PCDDs, PCDFs and non-ortho PCBs only were quantitatively analyzed, and recovery rates thereof were calculated. Also, lock mass fluctuation was examined.

TABLE 6

| | | Recovery rate (%) Example | |
|---|---|---|---|
| | | 7 | 8 |
| PCDDs | $^{13}C_{12}$-2,3,7,8-TeCDD | 91 | 97 |
| | $^{13}C_{12}$-1,2,3,7,8-PeCDD | 103 | 94 |
| | $^{13}C_{12}$-1,2,3,4,7,8-HxCDD | 97 | 101 |
| | $^{13}C_{12}$-1,2,3,6,7,8-HxCDD | 93 | 96 |
| | $^{13}C_{12}$-1,2,3,7,8,9-HxCDD | 94 | 102 |
| | $^{13}C_{12}$-1,2,3,4,6,7,8-HpCDD | 94 | 90 |
| | $^{13}C_{12}$-OCDD | 83 | 89 |
| PCDFs | $^{13}C_{12}$-2,3,7,8-TeCDF | 96 | 99 |
| | $^{13}C_{12}$-1,2,3,7,8-PeCDF | 103 | 98 |
| | $^{13}C_{12}$-2,3,4,7,8-PeCDF | 98 | 97 |
| | $^{13}C_{12}$-1,2,3,4,7,8-HxCDF | 98 | 96 |
| | $^{13}C_{12}$-1,2,3,6,7,8-HxCDF | 100 | 92 |
| | $^{13}C_{12}$-1,2,3,7,8,9-HxCDF | 95 | 96 |
| | $^{13}C_{12}$-2,3,4,6,7,8-HxCDF | 96 | 95 |
| | $^{13}C_{12}$-1,2,3,4,6,7,8-HpCDF | 97 | 85 |
| | $^{13}C_{12}$-1,2,3,4,7,8,9-HpCDF | 96 | 93 |
| | $^{13}C_{12}$-OCDF | 91 | 88 |

TABLE 6-continued

|  |  | Recovery rate (%) Example | |
|---|---|---|---|
|  |  | 7 | 8 |
| Non-ortho PCBs | $^{13}C_{12}$-3,4,4',5-TeCB (#81) | 114 | 98 |
|  | $^{13}C_{12}$-3,3',4,4'-TeCB (#77) | 111 | 101 |
|  | $^{13}C_{12}$-3,3',4,4',5-PeCB (#126) | 114 | 107 |
|  | $^{13}C_{12}$-3,3',4,4',5,5'-HxCB (#169) | 110 | 109 |

According to Table 6, recovery rates of PCDDs, PCDFs and non-ortho PCBs are high. Also, substantial lock mass fluctuation was not observed. The results reveal that liquid paraffin passes through the adsorption layer without being adsorbed to the adsorption layer, and is then disposed of, and thus does not interfere with extraction and quantification of the above dioxins.

Examples 9 to 12

Using the preparation device for an analytical sample of dioxins shown in FIG. 1, dioxins contained in the fish oil sample was extracted. As to the specifications of the fractionating tool used in the preparation device, the purification layer is the same as those in Examples 1 to 6, and the adsorption layer is as follows.
Adsorption Layer:

In a small-diameter portion of a tubular body same as those used in Examples 1 to 6, as shown in FIG. 1, 0.25 g (packing height: 25 mm) of graphite-containing silica gel and 0.065 g (packing height: 5 mm) of activated carbon-containing silica gel were packed to form a first adsorption layer, and 0.77 g (packing height: 30 mm) of alumina was packed to form a second adsorption layer. The proportion of activated carbon contained in activated carbon-containing silica gel, the proportion of graphite contained in graphite-containing silica gel, and the stacking ratio (volume ratio) between the activated carbon-containing silica gel layer and the graphite-containing silica gel layer in the first adsorption layer are as shown in Table 7.

In an extraction operation of dioxins, about 4 mL of a fish oil sample solution was added to the silver nitrate silica gel layer of the purification layer, and the purification layer was heated to 60° C. Then, 85 mL of n-hexane was gradually supplied to the purification layer, and the supplied n-hexane was allowed to pass through the purification layer and the adsorption layer. After n-hexane had passed through the adsorption layer, compressed air was allowed to pass therethrough for a drying treatment of the adsorption layer. Then, after heating the alumina layer of the second adsorption layer to 90° C., 1.0 mL of toluene was supplied to the adsorption layer from the side of the second adsorption layer, and toluene having passed through the second adsorption layer was recovered through the second branch channel to obtain a first analytical sample. Next, after heating the first adsorption layer to 90° C., 1.5 mL of toluene was supplied to the adsorption layer from the side of the second adsorption layer, and toluene having passed through the second adsorption layer and the first adsorption layer in this order was recovered through the first branch channel to obtain a second analytical sample. The time consumed to obtain the second analytical sample from addition of the fish oil sample was about 2 hours. Examples 13 and 14 to be described later demonstrated the same result of time consumption in obtaining the second analytical sample.

The first analytical sample and the second analytical sample were individually quantitatively analyzed by the HRGC/HRMS method, and recovery rates of dioxins and non-DL-PCBs were calculated. The results are shown in Table 8.

Example 13

Dioxins contained in the fish oil sample were extracted in the same manner as in Example 12 except that a fractionating tool in which the stacking order of the silver nitrate silica gel layer and the sulfuric acid silica gel layer was reversed was used in the purification layer, and the temperature of the purification layer was kept at room temperature (20° C.), to obtain a first analytical sample and a second analytical sample. Then, the first analytical sample and the second analytical sample were individually quantitatively analyzed by the HRGC/HRMS method, to calculate recovery rates of dioxins and non-DL-PCBs. The results are shown in Table 8.

Example 14

Using the preparation device for an analytical sample for dioxins shown in FIG. 3, dioxins contained in the fish oil sample were extracted. As to the specifications of the fractionating tool used in the preparation device, the purification layer is the same as those in Examples 1 to 6, and the adsorption layer is as follows.
Adsorption Layer:

In a small-diameter portion of a tubular body having an outer diameter of 8 mm, an inner diameter of 6 mm, and a length of 30 mm, as shown in FIG. 3, 0.25 g (packing height: 25 mm) of graphite-containing silica gel, 0.065 g (packing height: 5 mm) of activated carbon-containing silica gel and 0.77 g (packing height: 30 mm) of alumina were packed to form the layer. The proportion of activated carbon contained in the activated carbon-containing silica gel, the proportion of graphite contained in the graphite-containing silica gel, and the stacking ratio (volume ratio) between the activated carbon-containing silica gel layer and the graphite-containing silica gel layer were set as shown in Table 7.

In an extraction operation of dioxins, about 4 mL of the fish oil sample solution was added to the silver nitrate silica gel layer of the purification layer, and the purification layer was heated to 60° C. Then, 85 mL of n-hexane was gradually supplied to the purification layer, and the supplied n-hexane was allowed to pass through the purification layer and the adsorption layer. After n-hexane had passed through the adsorption layer, compressed air was allowed to pass therethrough for a drying treatment of the adsorption layer. Then, in the condition that the alumina layer of the adsorption layer was kept at room temperature (25° C.), 1.5 mL of a mixed solvent of n-hexane containing 50% by weight of dichloromethane was supplied from the side of the activated carbon-containing silica gel layer of the adsorption layer, and the mixed solvent having passed through the alumina layer of the adsorption layer was recovered to obtain a first analytical sample. Then, the activated carbon-containing silica gel layer and the graphite-containing silica gel layer of the adsorption layer were heated at 90° C., and 1.5 mL of toluene was supplied to the adsorption layer from the side of the alumina layer, and toluene having passed through the adsorption layer was recovered through the first branch channel to obtain a second analytical sample.

The first analytical sample and the second analytical sample were individually quantitatively analyzed by the HRGC/HRMS method, and recovery rates of dioxins and non-DL-PCBs were calculated. The results are shown in Table 8.

TABLE 7

| Example | Proportion of activated carbon (*1) (% by weight) | Proportion of graphite (*2) (% by weight) | Volume ratio (*3) |
|---|---|---|---|
| 9  | 0.13 | 5    | 1:5 |
| 10 | 0.13 | 12.5 | 1:5 |
| 11 | 0.13 | 25   | 1:5 |
| 12 | 0.13 | 50   | 1:5 |
| 13 | 0.13 | 50   | 1:5 |
| 14 | 0.13 | 50   | 1:5 |

(*1) Proportion of activated carbon contained in activated carbon-containing silica gel
(*2) Proportion of graphite contained in graphite-containing silica gel
(*3) Volume ratio (A:B) between activated carbon-containing silica gel layer (A) and graphite-containing silica gel layer (B)

the adequate range (60 to 120%) required by the regulation, and accordingly is well suited for quantitative analysis of mono-ortho PCBs together with the EU regulation target non-DL-PCBs.

In the second analytical sample, since a substantial interference peak by PCDE was not observed in the quantification according to the HRGC/HRMS method, it is considered that PCDE was effectively removed therefrom.

The present invention can be carried out in other specific forms without departing from the spirit or essential properties thereof. The above embodiments and examples are therefore to be considered in all respects as illustrative and not restrictive. The scope of the present invention is indicated by the appended claims rather than by the foregoing description. All changes and modifications which come within the range of equivalency of the claims are therefore intended to be included within the scope of the present invention.

TABLE 8

| | | | Recovery rate (%) Example | | | | | |
|---|---|---|---|---|---|---|---|---|
| | | | 9 | 10 | 11 | 12 | 13 | 14 |
| Second analytical sample | PCDDs | $^{13}C_{12}$-2,3,7,8-TeCDD | 95 | 88 | 95 | 97 | 97 | 90 |
| | | $^{13}C_{12}$-1,2,3,7,8-PeCDD | 89 | 88 | 99 | 100 | 102 | 83 |
| | | $^{13}C_{12}$-1,2,3,4,7,8-HxCDD | 93 | 98 | 90 | 100 | 102 | 84 |
| | | $^{13}C_{12}$-1,2,3,6,7,8-HxCDD | 89 | 95 | 90 | 94 | 107 | 88 |
| | | $^{13}C_{12}$-1,2,3,7,8,9-HxCDD | 90 | 100 | 89 | 97 | 107 | 93 |
| | | $^{13}C_{12}$-1,2,3,4,6,7,8-HpCDD | 89 | 95 | 82 | 97 | 92 | 93 |
| | | $^{13}C_{12}$-OCDD | 83 | 87 | 85 | 79 | 88 | 92 |
| | PCDFs | $^{13}C_{12}$-2,3,7,8-TeCDF | 102 | 95 | 98 | 99 | 98 | 88 |
| | | $^{13}C_{12}$-1,2,3,7,8-PeCDF | 94 | 96 | 99 | 105 | 100 | 84 |
| | | $^{13}C_{12}$-2,3,4,7,8-PeCDF | 93 | 94 | 98 | 100 | 100 | 89 |
| | | $^{13}C_{12}$-1,2,3,4,7,8-HxCDF | 94 | 95 | 89 | 101 | 104 | 90 |
| | | $^{13}C_{12}$-1,2,3,6,7,8-HxCDF | 94 | 96 | 89 | 93 | 103 | 92 |
| | | $^{13}C_{12}$-1,2,3,7,8,9-HxCDF | 93 | 95 | 91 | 91 | 101 | 101 |
| | | $^{13}C_{12}$-2,3,4,6,7,8-HxCDF | 95 | 94 | 88 | 97 | 100 | 91 |
| | | $^{13}C_{12}$-1,2,3,4,6,7,8-HpCDF | 85 | 89 | 82 | 94 | 97 | 84 |
| | | $^{13}C_{12}$-1,2,3,4,7,8,9-HpCDF | 93 | 90 | 89 | 96 | 94 | 92 |
| | | $^{13}C_{12}$-OCDF | 86 | 88 | 88 | 81 | 82 | 94 |
| | Non-ortho PCBs | $^{13}C_{12}$-3,4,4',5-TeCB (#81) | 82 | 87 | 95 | 99 | 97 | 93 |
| | | $^{13}C_{12}$-3,3',4,4'-TeCB (#77) | 90 | 86 | 93 | 98 | 96 | 95 |
| | | $^{13}C_{12}$-3,3',4,4',5-PeCB (#126) | 93 | 83 | 103 | 93 | 97 | 105 |
| | | $^{13}C_{12}$-3,3',4,4',5,5'-HxCB (#169) | 84 | 83 | 104 | 91 | 100 | 102 |
| First analytical sample | Mono-ortho PCBs | $^{13}C_{12}$-2',3,4,4',5-PeCB (#123) | 91 | 84 | 84 | 90 | 82 | 85 |
| | | $^{13}C_{12}$-2,3,4,4',5-PeCB (#118) | 95 | 95 | 95 | 97 | 81 | 84 |
| | | $^{13}C_{12}$-2,3,3',4,4'-PeCB (#105) | 97 | 85 | 85 | 81 | 85 | 90 |
| | | $^{13}C_{12}$-2,3,4,4',5-PeCB (#114) | 96 | 84 | 84 | 90 | 85 | 88 |
| | | $^{13}C_{12}$-2,3',4,4',5,5'-HxCB (#167) | 92 | 82 | 82 | 81 | 89 | 92 |
| | | $^{13}C_{12}$-2,3,3',4,4',5-HxCB (#156) | 94 | 91 | 91 | 97 | 91 | 92 |
| | | $^{13}C_{12}$-2,3,3',4,4',5'-HxCB (#157) | 103 | 97 | 97 | 96 | 86 | 86 |
| | | $^{13}C_{12}$-2,3,3',4,4',5,5'-HpCB (#189) | 86 | 84 | 84 | 95 | 89 | 97 |
| | Non-DL-PCBs | $^{13}C_{12}$-4-MoCB (#3) | 69 | 78 | 68 | 0 | 0 | 62 |
| | | $^{13}C_{12}$-4,4'-DiCB (#15) | 66 | 87 | 79 | 0 | 0 | 80 |
| | | $^{13}C_{12}$-2,4,4'-TrCB (#28) | 91 | 95 | 97 | 94 | 94 | 91 |
| | | $^{13}C_{12}$-2,2',5,5'-TeCB (#52) | 87 | 96 | 106 | 90 | 82 | 90 |
| | | $^{13}C_{12}$-2,3',4,4',5-PeCB (#118) | 84 | 99 | 89 | 100 | 95 | 102 |
| | | $^{13}C_{12}$-2,2',4,4',5,5'-HxCB (#153) | 89 | 63 | 79 | 86 | 80 | 90 |
| | | $^{13}C_{12}$-2,2',3,4,4',5,5'-HpCB (#180) | 119 | 102 | 99 | 102 | 102 | 103 |
| | | $^{13}C_{12}$-2,2',3,3',4,4',5,5'-OcCB (#194) | 84 | 102 | 96 | 101 | 103 | 99 |

According to Table 8, the second analytical sample contains PCDDs, PCDFs and non-ortho PCBs at high recovery rates. On the other hand, the first analytical sample contains mono-ortho PCBs at high recovery rates. The results reveal that in Examples 9 to 14, the dioxin group including non-ortho PCBs, PCDDs and PCDFs was separated from mono-ortho PCBs at high accuracy.

Table 8 also demonstrates that the first analytical sample obtained in Examples 9 to 14 contains non-DL-PCBs which are targets of the EU food regulation at recovery rates within

The invention claimed is:

1. A method for fractionating dioxins, comprising the step of:

passing an aliphatic hydrocarbon solvent solution of dioxins comprising mono-ortho PCBs and one or more selected from the group consisting of non-ortho PCBs, PCDDs and PCDFs through an activated carbon-containing silica gel layer and a graphite-containing silica gel layer in this order to separate the mono-ortho PCBs from the one or more selected from the group consisting of non-ortho PCBs, PCDDs and PCDFs,
wherein the ratio between the activated carbon-containing silica gel and the graphite-containing silica gel is 1:1 to 1:12 by volume.

2. The method for fractionating dioxins according to claim 1, wherein the aliphatic hydrocarbon solvent solution having passed through the graphite-containing silica gel layer is further passed through an alumina layer.

3. The method for fractionating dioxins according to claim 2, further comprising the steps of:
supplying the activated carbon-containing silica gel layer and the graphite-containing silica gel layer through which the aliphatic hydrocarbon solvent solution has passed with a solvent capable of dissolving dioxins, to secure the solvent having passed through the activated carbon-containing silica gel layer and the graphite-containing silica gel layer; and
supplying the alumina layer through which the aliphatic hydrocarbon solvent solution has passed with a solvent capable of dissolving dioxins, to secure the solvent having passed through the alumina layer.

4. A method for preparing a sample for analyzing dioxins contained in a solution of dioxins comprising mono-ortho PCBs and one or more selected from the group consisting of non-ortho PCBs, PCDDs and PCDFs, the method comprising the steps of:
adding the solution of dioxins to a purification layer including a silver nitrate silica gel layer and a sulfuric acid silica gel layer;
supplying the purification layer to which the solution of dioxins has been added with an aliphatic hydrocarbon solvent;
passing the aliphatic hydrocarbon solvent having passed through the purification layer through an activated carbon-containing silica gel layer and a graphite-containing silica gel layer in this order to separate the mono-ortho PCBs from the one or more selected from the group consisting of non-ortho PCBs, PCDDs and PCDFs;
passing the aliphatic hydrocarbon solvent having passed through the graphite-containing silica gel layer through an alumina layer;
supplying the alumina layer through which the aliphatic hydrocarbon solvent has passed with a solvent capable of dissolving dioxins, to secure the solvent having passed through the alumina layer as a first analytical sample; and
supplying the activated carbon-containing silica gel layer and the graphite-containing silica gel layer through which the aliphatic hydrocarbon solvent has passed with a solvent capable of dissolving dioxins, to secure the solvent having passed through the activated carbon-containing silica gel layer and the graphite-containing silica gel layer as a second analytical sample,
wherein the ratio between the activated carbon-containing silica gel and the graphite-containing silica gel is 1:1 to 1:12 by volume.

5. The method for preparing a sample for analyzing dioxins according to claim 4, wherein the solution of dioxins is added to the silver nitrate silica gel layer of the purification layer.

6. A method for analyzing dioxins contained in a solution of dioxins, comprising the step of:
analyzing a first analytical sample and a second analytical sample prepared by the method for preparing a sample for analyzing dioxins according to claim 4, by a gas chromatography method or a bioassay method.

* * * * *